US009713652B2

(12) United States Patent
Schoenfisch et al.

(10) Patent No.: US 9,713,652 B2
(45) Date of Patent: Jul. 25, 2017

(54) NITRIC OXIDE-RELEASING S-NITROSOTHIOL-MODIFIED SILICA PARTICLES AND METHODS OF MAKING THE SAME

(71) Applicants: Novan, Inc., Durham, NC (US); The University of North Carolina at Chapel Hill, Chapel Hill, NC (US)

(72) Inventors: Mark Schoenfisch, Chapel Hill, NC (US); Daniel Riccio, Raleigh, NC (US); Julia Nugent, Durham, NC (US); Nathan Stasko, Durham, NC (US)

(73) Assignees: The University of North Carolina at Chapel Hill, Chapel Hill, NC (US); Novan, Inc., Morrisville, NC (US)

( * ) Notice: Subject to any disclaimer, the term of this patent is extended or adjusted under 35 U.S.C. 154(b) by 381 days.

(21) Appl. No.: 13/975,930

(22) Filed: Aug. 26, 2013

(65) Prior Publication Data
US 2013/0344334 A1    Dec. 26, 2013

Related U.S. Application Data

(63) Continuation of application No. PCT/US2012/026960, filed on Feb. 28, 2012.
(Continued)

(51) Int. Cl.
*C08K 3/28* (2006.01)
*C08K 3/30* (2006.01)
(Continued)

(52) U.S. Cl.
CPC ............. *A61L 2/18* (2013.01); *C07F 7/0874* (2013.01); *C07F 7/10* (2013.01); *C07F 7/1836* (2013.01);
(Continued)

(58) Field of Classification Search
CPC ....... C08K 3/28; C08K 3/30; C08K 2003/023
(Continued)

(56) References Cited

U.S. PATENT DOCUMENTS 4,507,466 A    3/1985    Tomalia et al.
4,558,120 A    12/1985   Tomalia et al.
(Continued)

FOREIGN PATENT DOCUMENTS

EP    0 805 678 B1    10/2003
EP    0 746 327 B1    4/2004
(Continued)

OTHER PUBLICATIONS

Frost et al., Synthesis, characterization, and controlled nitric oxide release from S-nitrosothiol-derivatized fumed silica polymer filler particles, Wiley Periodicals, J. Biomed. Mater. Res. 72A: 409-419, 2005.*

(Continued)

*Primary Examiner* — Holly Le
(74) *Attorney, Agent, or Firm* — Myers Bigel, P.A.

(57) ABSTRACT

Provided according to some embodiments of the invention are methods of forming co-condensed silica particles. In some embodiments, the methods include reacting a thiol-containing silane and a backbone alkoxysilane in a reaction solution that comprises water to form thiol-functionalized co-condensed silica particles, wherein the thiol-functionalized co-condensed silica particles include a polysiloxane matrix and at least some of thiol groups are present within the polysiloxane matrix; and reacting the thiol-functionalized co-condensed silica particles with a nitrosating agent to provide the S-nitrosothiol-functionalized co-condensed silica particles. In some embodiments, provided are S-nitrosothiol-functionalized co-condensed silica particles.

21 Claims, 12 Drawing Sheets

Related U.S. Application Data

(60) Provisional application No. 61/447,368, filed on Feb. 28, 2011, provisional application No. 61/565,694, filed on Dec. 1, 2011.

(51) Int. Cl.
*B32B 5/16* (2006.01)
*A61L 2/18* (2006.01)
*C07F 7/08* (2006.01)
*C07F 7/18* (2006.01)
*C08G 77/26* (2006.01)
*C08G 77/28* (2006.01)
*C07F 7/10* (2006.01)
*C08K 3/02* (2006.01)

(52) U.S. Cl.
CPC ............ *C08G 77/26* (2013.01); *C08G 77/28* (2013.01); *C08K 3/28* (2013.01); *C08K 3/30* (2013.01); *C08K 2003/023* (2013.01); *Y10T 428/2982* (2015.01)

(58) Field of Classification Search
USPC .................. 436/107, 119, 527; 428/403–405
See application file for complete search history.

(56) References Cited

U.S. PATENT DOCUMENTS

| | | |
|---|---|---|
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,713,975 A | 12/1987 | Tomalia et al. |
| 4,737,550 A | 4/1988 | Tomalia |
| 4,857,599 A | 8/1989 | Tomalia et al. |
| 4,871,779 A | 10/1989 | Killat et al. |
| 4,985,023 A | 1/1991 | Blank et al. |
| 4,990,338 A | 2/1991 | Blank et al. |
| 5,035,892 A | 7/1991 | Blank et al. |
| 5,045,322 A | 9/1991 | Blank et al. |
| 5,061,487 A | 10/1991 | Blank et al. |
| 5,079,004 A | 1/1992 | Blank et al. |
| 5,380,758 A | 1/1995 | Stamler et al. |
| 5,405,919 A | 4/1995 | Keefer et al. |
| 5,418,301 A | 5/1995 | Hult et al. |
| 5,428,070 A | 6/1995 | Cooke et al. |
| 5,504,117 A | 4/1996 | Gorfine |
| 5,519,020 A | 5/1996 | Smith et al. |
| 5,525,357 A | 6/1996 | Keefer et al. |
| 5,574,068 A | 11/1996 | Stamler et al. |
| 5,593,876 A | 1/1997 | Stamler et al. |
| 5,599,984 A | 2/1997 | Bianchi et al. |
| 5,629,322 A | 5/1997 | Guthikonda et al. |
| 5,632,981 A | 5/1997 | Saavedra et al. |
| 5,650,442 A | 7/1997 | Mitchell et al. |
| 5,650,447 A | 7/1997 | Keefer et al. |
| 5,665,077 A | 9/1997 | Rosen et al. |
| 5,676,963 A | 10/1997 | Keefer et al. |
| 5,691,423 A | 11/1997 | Smith et al. |
| 5,693,676 A | 12/1997 | Gorfine |
| 5,700,830 A | 12/1997 | Korthuis et al. |
| 5,718,892 A | 2/1998 | Keefer et al. |
| 5,726,156 A | 3/1998 | Girten et al. |
| 5,750,573 A | 5/1998 | Bianchi et al. |
| 5,753,684 A | 5/1998 | Bianchi et al. |
| 5,760,001 A | 6/1998 | Girten et al. |
| 5,770,645 A | 6/1998 | Stamler et al. |
| 5,786,332 A | 7/1998 | Girten et al. |
| 5,789,447 A | 8/1998 | Wink, Jr. et al. |
| 5,797,887 A | 8/1998 | Rosen et al. |
| 5,810,010 A | 9/1998 | Anbar |
| 5,814,666 A | 9/1998 | Green et al. |
| 5,814,667 A | 9/1998 | Mitchell et al. |
| 5,821,261 A | 10/1998 | Durette et al. |
| 5,837,736 A | 11/1998 | Mitchell et al. |
| 5,840,759 A | 11/1998 | Mitchell et al. |
| 5,849,794 A | 12/1998 | Bianchi et al. |
| 5,852,058 A | 12/1998 | Cooke et al. |
| 5,854,289 A | 12/1998 | Bianchi et al. |
| 5,859,062 A | 1/1999 | Bianchi et al. |
| 5,861,168 A | 1/1999 | Cooke et al. |
| 5,863,890 A | 1/1999 | Stamler et al. |
| 5,891,459 A | 4/1999 | Cooke et al. |
| 5,891,472 A | 4/1999 | Russell |
| 5,910,316 A | 6/1999 | Keefer et al. |
| 5,932,538 A | 8/1999 | Garvey et al. |
| 5,958,427 A | 9/1999 | Salzman et al. |
| 5,961,466 A | 10/1999 | Anbar |
| 5,962,520 A | 10/1999 | Smith et al. |
| 5,994,294 A | 11/1999 | Garvey et al. |
| 5,994,444 A | 11/1999 | Trescony et al. |
| 5,999,843 A | 12/1999 | Anbar |
| 6,008,255 A | 12/1999 | Bianchi et al. |
| 6,022,900 A | 2/2000 | Bianchi et al. |
| 6,035,225 A | 3/2000 | Anbar |
| 6,043,358 A | 3/2000 | Caldwell et al. |
| 6,045,827 A | 4/2000 | Russell |
| 6,070,928 A | 6/2000 | Campbell |
| 6,087,479 A | 7/2000 | Stamler et al. |
| 6,103,275 A | 8/2000 | Seitz et al. |
| 6,110,453 A | 8/2000 | Keefer et al. |
| 6,143,037 A | 11/2000 | Goldstein et al. |
| 6,147,068 A | 11/2000 | Smith et al. |
| 6,151,522 A | 11/2000 | Alfano et al. |
| 6,160,021 A | 12/2000 | Lerner et al. |
| 6,171,232 B1 | 1/2001 | Papandreou et al. |
| 6,174,539 B1 | 1/2001 | Stamler et al. |
| 6,180,082 B1 | 1/2001 | Woltering et al. |
| 6,180,676 B1 | 1/2001 | Bianchi et al. |
| 6,190,704 B1 | 2/2001 | Murrell |
| 6,200,558 B1 | 3/2001 | Saavedra et al. |
| 6,207,855 B1 | 3/2001 | Toone et al. |
| 6,218,016 B1 | 4/2001 | Tedeschi et al. |
| 6,232,336 B1 | 5/2001 | Hrabie et al. |
| 6,232,434 B1 | 5/2001 | Stamler et al. |
| 6,238,683 B1 | 5/2001 | Burnett et al. |
| 6,248,787 B1 | 6/2001 | Bianchi et al. |
| 6,255,277 B1 | 7/2001 | Stamler et al. |
| 6,261,594 B1 | 7/2001 | Smith et al. |
| 6,270,779 B1 | 8/2001 | Fitzhugh et al. |
| 6,287,601 B1 | 9/2001 | Russell |
| 6,290,981 B1 | 9/2001 | Keefer et al. |
| 6,291,424 B1 | 9/2001 | Stamler et al. |
| 6,294,517 B1 | 9/2001 | Garvey et al. |
| 6,299,980 B1 | 10/2001 | Shah et al. |
| 6,323,211 B1 | 11/2001 | Garvey et al. |
| 6,350,467 B1 | 2/2002 | Demopoulos et al. |
| 6,352,709 B1 | 3/2002 | Stamler et al. |
| 6,358,536 B1 | 3/2002 | Thomas |
| 6,359,167 B2 | 3/2002 | Toone et al. |
| 6,359,182 B1 | 3/2002 | Stamler et al. |
| 6,369,071 B1 | 4/2002 | Haj-Yehia |
| 6,372,733 B1 | 4/2002 | Caldwell et al. |
| 6,377,321 B1 | 4/2002 | Khan et al. |
| 6,379,660 B1 | 4/2002 | Saavedra et al. |
| 6,379,691 B1 | 4/2002 | Tedeschi et al. |
| 6,391,895 B1 | 5/2002 | Towart et al. |
| 6,403,759 B2 | 6/2002 | Stamler et al. |
| 6,410,622 B1 | 6/2002 | Endres |
| 6,417,162 B1 | 7/2002 | Garvey et al. |
| 6,432,077 B1 | 8/2002 | Stenzler |
| 6,433,182 B1 | 8/2002 | Garvey et al. |
| 6,436,975 B1 | 8/2002 | Del Soldato |
| 6,441,254 B1 | 8/2002 | Dobert |
| 6,448,267 B1 | 9/2002 | Anggard et al. |
| 6,451,337 B1 | 9/2002 | Smith et al. |
| 6,455,542 B1 | 9/2002 | Anggard et al. |
| 6,469,065 B1 | 10/2002 | Garvey et al. |
| 6,471,978 B1 | 10/2002 | Stamler et al. |
| 6,472,390 B1 | 10/2002 | Stamler et al. |
| 6,488,951 B2 | 12/2002 | Toone et al. |
| 6,492,405 B2 | 12/2002 | Haj-Yehia |
| 6,511,991 B2 | 1/2003 | Hrabie et al. |

(56) References Cited

U.S. PATENT DOCUMENTS

| | | |
|---|---|---|
| 6,514,934 B1 | 2/2003 | Garvey et al. |
| 6,538,033 B2 | 3/2003 | Bing |
| 6,560,478 B1 | 5/2003 | Alfano et al. |
| 6,562,344 B1 | 5/2003 | Stamler et al. |
| 6,562,785 B1 | 5/2003 | Shapiro |
| 6,583,113 B2 | 6/2003 | Stamler et al. |
| 6,583,311 B2 | 6/2003 | Toone et al. |
| 6,605,447 B2 | 8/2003 | Weiss et al. |
| 6,610,660 B1 | 8/2003 | Saavedra et al. |
| 6,627,602 B2 | 9/2003 | Stamler et al. |
| 6,642,208 B2 | 11/2003 | Cooke et al. |
| 6,642,260 B2 | 11/2003 | Haj-Yehia |
| 6,645,518 B2 | 11/2003 | Tedeschi et al. |
| 6,646,006 B2 | 11/2003 | Cooke et al. |
| 6,656,217 B1 | 12/2003 | Herzog, Jr. et al. |
| 6,673,338 B1 | 1/2004 | Arnold et al. |
| 6,673,891 B2 | 1/2004 | Stamler et al. |
| 6,699,846 B2 | 3/2004 | Elliott et al. |
| 6,703,046 B2 | 3/2004 | Fitzhugh et al. |
| 6,706,274 B2 | 3/2004 | Herrmann et al. |
| 6,709,681 B2 | 3/2004 | Benjamin et al. |
| 6,723,703 B2 | 4/2004 | Gaston et al. |
| 6,737,447 B1 | 5/2004 | Smith et al. |
| 6,747,062 B2 | 6/2004 | Murrell |
| 6,750,254 B2 | 6/2004 | Hrabie et al. |
| 6,758,214 B2 | 7/2004 | Fine et al. |
| 6,759,430 B2 | 7/2004 | Anggard et al. |
| 6,780,849 B2 | 8/2004 | Herrmann et al. |
| 6,793,644 B2 | 9/2004 | Stenzler |
| 6,796,966 B2 | 9/2004 | Thomas |
| 6,841,166 B1 | 1/2005 | Zhang et al. |
| 6,855,366 B2 | 2/2005 | Smith et al. |
| 6,875,840 B2 | 4/2005 | Stamler et al. |
| 6,887,485 B2 | 5/2005 | Fitzhugh et al. |
| 6,887,994 B2 | 5/2005 | Stamler et al. |
| 6,894,073 B2 | 5/2005 | Lee et al. |
| 6,896,899 B2 | 5/2005 | Demopolos et al. |
| 6,897,218 B2 | 5/2005 | Casella et al. |
| 6,911,433 B2 | 6/2005 | Saavedra et al. |
| 6,911,478 B2 | 6/2005 | Hrabie et al. |
| 6,946,484 B2 | 9/2005 | Adams et al. |
| 6,949,530 B2 | 9/2005 | Hrabie et al. |
| 6,951,902 B2 | 10/2005 | McDonald et al. |
| 6,964,984 B2 | 11/2005 | Stamler et al. |
| 6,974,801 B2 | 12/2005 | Honda et al. |
| 7,012,098 B2 | 3/2006 | Manning et al. |
| 7,015,347 B2 | 3/2006 | Toone et al. |
| 7,025,869 B2 | 4/2006 | Fine et al. |
| 7,030,238 B2 | 4/2006 | Stamler et al. |
| 7,033,999 B2 | 4/2006 | Stamler et al. |
| 7,040,313 B2 | 5/2006 | Fine et al. |
| 7,048,951 B1 | 5/2006 | Seitz et al. |
| 7,049,308 B2 | 5/2006 | Stamler et al. |
| 7,052,711 B2 | 5/2006 | West et al. |
| 7,070,798 B1 | 7/2006 | Michal et al. |
| 7,081,524 B2 | 7/2006 | Saavedra et al. |
| 7,087,588 B2 | 8/2006 | Del Soldato |
| 7,087,709 B2 | 8/2006 | Stamler et al. |
| 7,122,018 B2 | 10/2006 | Stenzler et al. |
| 7,122,027 B2 | 10/2006 | Trescony et al. |
| 7,122,529 B2 | 10/2006 | Ruane et al. |
| 7,128,904 B2 | 10/2006 | Batchelor et al. |
| 7,135,189 B2 | 11/2006 | Knapp |
| 7,135,498 B1 | 11/2006 | Chopp et al. |
| 7,157,500 B2 | 1/2007 | Stamler et al. |
| 7,169,809 B2 | 1/2007 | Berthelette et al. |
| 7,176,237 B2 | 2/2007 | Honda et al. |
| 7,179,475 B2 | 2/2007 | Burnett et al. |
| 7,189,761 B2 | 3/2007 | Gorfine |
| 7,199,154 B2 | 4/2007 | Berthelette et al. |
| 7,204,980 B2 | 4/2007 | Clark |
| 7,226,586 B2 | 6/2007 | Fitzhugh et al. |
| 7,234,079 B2 | 6/2007 | Cheng |
| 7,259,250 B2 | 8/2007 | Stamler et al. |
| 7,279,176 B1 | 10/2007 | West et al. |
| 7,282,519 B2 | 10/2007 | Garvey et al. |
| 7,314,857 B2 | 1/2008 | Madhyastha |
| 7,335,383 B2 | 2/2008 | Meyerhoff et al. |
| 7,345,053 B2 | 3/2008 | Garvey |
| 7,348,319 B2 | 3/2008 | Hrabie et al. |
| 7,364,585 B2 | 4/2008 | Weber |
| 7,396,829 B2 | 7/2008 | Garvey et al. |
| 7,417,109 B2 | 8/2008 | Stamler et al. |
| 7,425,218 B2 | 9/2008 | Keefer et al. |
| 7,432,301 B2 | 10/2008 | Gaston et al. |
| 7,452,916 B2 | 11/2008 | Cooke |
| 7,468,435 B2 | 12/2008 | Waterhouse et al. |
| 7,485,324 B2 | 2/2009 | Miller et al. |
| 7,520,866 B2 | 4/2009 | Stenzler et al. |
| 7,531,164 B2 | 5/2009 | Daaka et al. |
| 7,569,559 B2 | 8/2009 | Arnold et al. |
| 7,582,623 B2 | 9/2009 | Mascharak |
| 7,595,313 B2 | 9/2009 | Garvey et al. |
| 7,622,501 B2 | 11/2009 | Dufresne et al. |
| 7,622,502 B2 | 11/2009 | Berthelette et al. |
| 7,645,748 B2 | 1/2010 | Orchansky et al. |
| 7,645,749 B2 | 1/2010 | Orchansky et al. |
| 7,651,697 B2 | 1/2010 | West et al. |
| 7,655,423 B2 | 2/2010 | Chopp et al. |
| 7,678,391 B2 | 3/2010 | Graham et al. |
| 7,678,830 B2 | 3/2010 | Honda et al. |
| 7,696,247 B2 | 4/2010 | Herrmann et al. |
| 7,745,656 B2 | 6/2010 | Toone et al. |
| 7,763,283 B2 | 7/2010 | Batchelor et al. |
| 7,785,616 B2 | 8/2010 | Stamler et al. |
| 7,795,286 B2 | 9/2010 | Lucet-Levannier |
| 7,799,335 B2 | 9/2010 | Herrmann et al. |
| 7,807,716 B2 | 10/2010 | Farber |
| 7,811,600 B2 | 10/2010 | Cheng et al. |
| 7,820,284 B2 | 10/2010 | Terry |
| 7,829,553 B2 | 11/2010 | Arnold et al. |
| 7,838,023 B2 | 11/2010 | Garvey et al. |
| 7,846,400 B2 | 12/2010 | Hyde et al. |
| 7,862,598 B2 | 1/2011 | Hyde et al. |
| 7,892,198 B2 | 2/2011 | Stenzler |
| 7,897,399 B2 | 3/2011 | Hyde et al. |
| 7,928,079 B2 | 4/2011 | Hrabie et al. |
| 7,928,096 B2 | 4/2011 | Waterhouse et al. |
| 7,947,299 B2 | 5/2011 | Knapp |
| 7,972,137 B2 | 7/2011 | Rosen |
| 7,975,699 B2 | 7/2011 | Hyde et al. |
| 8,003,811 B2 | 8/2011 | Almirante |
| 8,017,074 B2 | 9/2011 | Arnold |
| 8,021,679 B2 | 9/2011 | Chen |
| 8,034,384 B2 | 10/2011 | Meyerhoff |
| 8,043,246 B2 | 10/2011 | Av-Gay et al. |
| 2001/0012851 A1 | 8/2001 | Lundy et al. |
| 2001/0025057 A1 | 9/2001 | Gorfine |
| 2001/0038832 A1 | 11/2001 | Bonavida et al. |
| 2001/0053772 A1 | 12/2001 | Bonavida et al. |
| 2002/0028851 A1 | 3/2002 | Bianchi et al. |
| 2002/0049157 A1 | 4/2002 | Wu et al. |
| 2002/0061879 A1 | 5/2002 | Garvey et al. |
| 2002/0068365 A1 | 6/2002 | Kuhrts |
| 2002/0090401 A1 | 7/2002 | Tucker et al. |
| 2002/0115586 A1 | 8/2002 | Enikolopov |
| 2002/0132234 A1 | 9/2002 | Moskowitz |
| 2002/0136763 A1 | 9/2002 | Demopoulos et al. |
| 2002/0138051 A1 | 9/2002 | Hole et al. |
| 2002/0143007 A1 | 10/2002 | Garvey et al. |
| 2002/0143062 A1 | 10/2002 | Lopez-Berestein et al. |
| 2002/0155174 A1 | 10/2002 | Benjamin et al. |
| 2002/0161042 A1 | 10/2002 | Gorfine |
| 2003/0027844 A1 | 2/2003 | Soldato |
| 2003/0039697 A1 | 2/2003 | Zhao et al. |
| 2003/0050305 A1 | 3/2003 | Tejada |
| 2003/0072783 A1 | 4/2003 | Stamler et al. |
| 2003/0093143 A1 | 5/2003 | Zhao et al. |
| 2003/0134779 A1 | 7/2003 | Diarra et al. |
| 2003/0170674 A1 | 9/2003 | Moskowitz |
| 2003/0203915 A1 | 10/2003 | Fang et al. |
| 2003/0205234 A1 | 11/2003 | Bardach et al. |
| 2004/0009238 A1 | 1/2004 | Miller et al. |
| 2004/0013747 A1 | 1/2004 | Tucker et al. |

(56) References Cited

U.S. PATENT DOCUMENTS

| | | |
|---|---|---|
| 2004/0033480 A1 | 2/2004 | Wong |
| 2004/0037836 A1 | 2/2004 | Stamler et al. |
| 2004/0037897 A1 | 2/2004 | Benjamin et al. |
| 2004/0043068 A1 | 3/2004 | Tedeschi et al. |
| 2004/0076582 A1 | 4/2004 | Dimatteo et al. |
| 2004/0082659 A1 | 4/2004 | Cooke et al. |
| 2004/0105898 A1 | 6/2004 | Benjamin et al. |
| 2004/0110691 A1 | 6/2004 | Stamler |
| 2004/0131703 A1 | 7/2004 | Bach et al. |
| 2004/0143010 A1 | 7/2004 | Esteve-Soler et al. |
| 2004/0147598 A1 | 7/2004 | Haj-Yehia |
| 2004/0157936 A1 | 8/2004 | Burnett et al. |
| 2004/0228889 A1 | 11/2004 | Cals-Grierson |
| 2004/0254419 A1 | 12/2004 | Wang et al. |
| 2004/0265244 A1 | 12/2004 | Rosen |
| 2005/0036949 A1 | 2/2005 | Tucker et al. |
| 2005/0037093 A1 | 2/2005 | Benjamin |
| 2005/0054714 A1 | 3/2005 | Munoz et al. |
| 2005/0065161 A1 | 3/2005 | Garvey et al. |
| 2005/0069595 A1 | 3/2005 | Chen et al. |
| 2005/0074506 A1 | 4/2005 | Natan et al. |
| 2005/0079132 A1 | 4/2005 | Wang et al. |
| 2005/0080021 A1 | 4/2005 | Tucker et al. |
| 2005/0080024 A1 | 4/2005 | Tucker et al. |
| 2005/0131064 A1 | 6/2005 | Gaston et al. |
| 2005/0142217 A1 | 6/2005 | Adams et al. |
| 2005/0142218 A1 | 6/2005 | Tucker et al. |
| 2005/0152891 A1 | 7/2005 | Toone et al. |
| 2005/0165452 A1 | 7/2005 | Sigg et al. |
| 2005/0171066 A1 | 8/2005 | Shami |
| 2005/0171199 A1 | 8/2005 | Murrell |
| 2005/0187222 A1 | 8/2005 | Garvey et al. |
| 2005/0220838 A1 | 10/2005 | Zhao et al. |
| 2005/0249818 A1 | 11/2005 | Sawan et al. |
| 2005/0265958 A1 | 12/2005 | West et al. |
| 2005/0281867 A1 | 12/2005 | Kahn et al. |
| 2006/0008529 A1 | 1/2006 | Meyerhoff et al. |
| 2006/0009431 A1 | 1/2006 | Earl et al. |
| 2006/0035854 A1 | 2/2006 | Goldstein et al. |
| 2006/0039950 A1 | 2/2006 | Zhou et al. |
| 2006/0058363 A1 | 3/2006 | Wang et al. |
| 2006/0067909 A1 | 3/2006 | West et al. |
| 2006/0095120 A1 | 5/2006 | Hermann |
| 2006/0100159 A1 | 5/2006 | Stamler et al. |
| 2006/0142183 A1 | 6/2006 | Diarra et al. |
| 2006/0147553 A1 | 7/2006 | Miller et al. |
| 2006/0147904 A1 | 7/2006 | Wong |
| 2006/0159726 A1 | 7/2006 | Shell |
| 2006/0172018 A1 | 8/2006 | Fine et al. |
| 2006/0198831 A1 | 9/2006 | Stamler et al. |
| 2006/0211601 A1 | 9/2006 | Stamler et al. |
| 2006/0269620 A1 | 11/2006 | Morris et al. |
| 2006/0286158 A1 | 12/2006 | Calvert Murrell et al. |
| 2006/0286159 A1 | 12/2006 | Calvert Murrell et al. |
| 2007/0003538 A1 | 1/2007 | Madhyastha |
| 2007/0014686 A1 | 1/2007 | Arnold et al. |
| 2007/0014733 A1 | 1/2007 | O'Donnell et al. |
| 2007/0014828 A1 | 1/2007 | Fitzhugh et al. |
| 2007/0037821 A1 | 2/2007 | Garvey et al. |
| 2007/0048344 A1 | 3/2007 | Yahiaoui et al. |
| 2007/0053952 A1 | 3/2007 | Chen et al. |
| 2007/0053955 A1 | 3/2007 | Larson et al. |
| 2007/0053966 A1 | 3/2007 | Ang et al. |
| 2007/0059351 A1 | 3/2007 | Murrell et al. |
| 2007/0086954 A1 | 4/2007 | Miller |
| 2007/0087025 A1 | 4/2007 | Fitzhugh et al. |
| 2007/0088345 A1 | 4/2007 | Larson et al. |
| 2007/0089739 A1 | 4/2007 | Fine et al. |
| 2007/0116785 A1 | 5/2007 | Miller |
| 2007/0129690 A1 | 6/2007 | Rosenblatt et al. |
| 2007/0148136 A1 | 6/2007 | Whitlock |
| 2007/0154570 A1 | 7/2007 | Miller et al. |
| 2007/0166227 A1 | 7/2007 | Liu et al. |
| 2007/0172469 A1 | 7/2007 | Clark |
| 2007/0191377 A1 | 8/2007 | Worcel |
| 2007/0196327 A1 | 8/2007 | Kalivretenos et al. |
| 2007/0197543 A1 | 8/2007 | Esteve-Soler et al. |
| 2007/0202155 A1 | 8/2007 | Ang et al. |
| 2007/0203242 A1 | 8/2007 | Calton |
| 2007/0207179 A1 | 9/2007 | Andersen et al. |
| 2007/0219208 A1 | 9/2007 | Kalyanaraman et al. |
| 2007/0225250 A1 | 9/2007 | Brown |
| 2007/0239107 A1 | 10/2007 | Lundberg et al. |
| 2007/0243262 A1 | 10/2007 | Hurley et al. |
| 2007/0248676 A1 | 10/2007 | Stamler et al. |
| 2007/0264225 A1 | 11/2007 | Cheng et al. |
| 2007/0270348 A1 | 11/2007 | Kahn et al. |
| 2007/0275100 A1 | 11/2007 | Miller |
| 2008/0025972 A1 | 1/2008 | Daaka et al. |
| 2008/0039521 A1 | 2/2008 | Yasuda et al. |
| 2008/0045909 A1 | 2/2008 | Fossel |
| 2008/0069848 A1 | 3/2008 | Peters |
| 2008/0069863 A1 | 3/2008 | Peters |
| 2008/0069905 A1 | 3/2008 | Peters |
| 2008/0071206 A1 | 3/2008 | Peters |
| 2008/0089956 A1 | 4/2008 | Da et al. |
| 2008/0139450 A1 | 6/2008 | Madhyastha et al. |
| 2008/0145449 A1 | 6/2008 | Stamler |
| 2008/0171021 A1 | 7/2008 | Bach et al. |
| 2008/0171351 A1 | 7/2008 | Smith |
| 2008/0175881 A1 | 7/2008 | Ippoliti et al. |
| 2008/0182797 A1 | 7/2008 | Nudler et al. |
| 2008/0193385 A1 | 8/2008 | Maibach |
| 2008/0193566 A1 | 8/2008 | Miller et al. |
| 2008/0207491 A1 | 8/2008 | Diarra et al. |
| 2008/0207713 A1 | 8/2008 | Wang et al. |
| 2008/0214646 A1 | 9/2008 | Knaus et al. |
| 2008/0226751 A1 | 9/2008 | Tucker et al. |
| 2008/0241208 A1 | 10/2008 | Shanley et al. |
| 2008/0275093 A1 | 11/2008 | Garvey et al. |
| 2008/0280984 A1 | 11/2008 | Fossel |
| 2008/0286321 A1 | 11/2008 | Reneker et al. |
| 2008/0287861 A1 | 11/2008 | Stenzler et al. |
| 2008/0311163 A1 | 12/2008 | Peters |
| 2008/0317626 A1 | 12/2008 | Arnold et al. |
| 2008/0317679 A1 | 12/2008 | Tamarkin et al. |
| 2009/0004298 A1 | 1/2009 | Gaston et al. |
| 2009/0010989 A1 | 1/2009 | Peters |
| 2009/0018091 A1 | 1/2009 | Ellis et al. |
| 2009/0028966 A1 | 1/2009 | Chen et al. |
| 2009/0036491 A1 | 2/2009 | Tucker et al. |
| 2009/0042819 A1 | 2/2009 | Ellis et al. |
| 2009/0048219 A1 | 2/2009 | Garvey |
| 2009/0069449 A1 | 3/2009 | Smith et al. |
| 2009/0081279 A1 | 3/2009 | Jezek et al. |
| 2009/0088411 A1 | 4/2009 | Renzi et al. |
| 2009/0093510 A1 | 4/2009 | Clementi et al. |
| 2009/0098187 A1 | 4/2009 | Peters et al. |
| 2009/0108777 A1 | 4/2009 | Hyde et al. |
| 2009/0110612 A1 | 4/2009 | Hyde et al. |
| 2009/0110712 A1 | 4/2009 | Hyde et al. |
| 2009/0110933 A1 | 4/2009 | Hyde et al. |
| 2009/0110958 A1 | 4/2009 | Hyde et al. |
| 2009/0112055 A1 | 4/2009 | Hyde et al. |
| 2009/0112193 A1 | 4/2009 | Hyde et al. |
| 2009/0112197 A1 | 4/2009 | Hyde et al. |
| 2009/0118819 A1 | 5/2009 | Merz et al. |
| 2009/0123528 A1 | 5/2009 | Fossel |
| 2009/0131342 A1 | 5/2009 | Ellis |
| 2009/0136410 A1 | 5/2009 | Smith |
| 2009/0137683 A1 | 5/2009 | Yasuda et al. |
| 2009/0143417 A1 | 6/2009 | Smith et al. |
| 2009/0148482 A1 | 6/2009 | Peters |
| 2009/0186859 A1 | 7/2009 | Velázquez et al. |
| 2009/0191284 A1 | 7/2009 | Conoci et al. |
| 2009/0196930 A1 | 8/2009 | Surber et al. |
| 2009/0197964 A1 | 8/2009 | Summar et al. |
| 2009/0203653 A1 | 8/2009 | Garvey |
| 2009/0214618 A1 | 8/2009 | Schoenfisch et al. |
| 2009/0214624 A1 | 8/2009 | Smith et al. |
| 2009/0214674 A1 | 8/2009 | Barraud et al. |
| 2009/0215838 A1 | 8/2009 | Garvey et al. |
| 2009/0221536 A1 | 9/2009 | Fossel |
| 2009/0222088 A1 | 9/2009 | Chen et al. |

(56) References Cited

U.S. PATENT DOCUMENTS

| | | |
|---|---|---|
| 2009/0226504 A1 | 9/2009 | Peters |
| 2009/0232863 A1 | 9/2009 | Cheng et al. |
| 2009/0232868 A1 | 9/2009 | Chen et al. |
| 2009/0255536 A1 | 10/2009 | Av-Gay et al. |
| 2009/0263416 A1 | 10/2009 | Dawson et al. |
| 2009/0264398 A1 | 10/2009 | Bauer |
| 2009/0270509 A1 | 10/2009 | Arnold et al. |
| 2009/0287072 A1 | 11/2009 | Meyerhoff et al. |
| 2009/0297634 A1 | 12/2009 | Friedman et al. |
| 2009/0304815 A1 | 12/2009 | Cossu et al. |
| 2009/0317885 A1 | 12/2009 | Mascharak |
| 2010/0003338 A1 | 1/2010 | Hubbell et al. |
| 2010/0015253 A1 | 1/2010 | Benjamin |
| 2010/0016790 A1 | 1/2010 | Peters |
| 2010/0021506 A1 | 1/2010 | Jones |
| 2010/0040703 A1 | 2/2010 | Miller et al. |
| 2010/0062055 A1 | 3/2010 | Herrmann et al. |
| 2010/0076162 A1 | 3/2010 | Ameer et al. |
| 2010/0086530 A1 | 4/2010 | Martinov |
| 2010/0087370 A1 | 4/2010 | Jain et al. |
| 2010/0099729 A1 | 4/2010 | Almirante et al. |
| 2010/0112033 A1 | 5/2010 | Ganzarolli De Oliveira et al. |
| 2010/0112095 A1 | 5/2010 | Morris et al. |
| 2010/0129474 A1 | 5/2010 | Benjamin et al. |
| 2010/0152683 A1 | 6/2010 | Lindgren et al. |
| 2010/0159119 A1 | 6/2010 | Chen et al. |
| 2010/0166603 A1 | 7/2010 | Opie |
| 2010/0178319 A1 | 7/2010 | Lindgren et al. |
| 2010/0184992 A1 | 7/2010 | Toone et al. |
| 2010/0196517 A1 | 8/2010 | Fossel |
| 2010/0197702 A1 | 8/2010 | Hellberg et al. |
| 2010/0197802 A1 | 8/2010 | Jezek et al. |
| 2010/0209469 A1 | 8/2010 | Bezwada |
| 2010/0221308 A1 | 9/2010 | Madhyastha et al. |
| 2010/0233304 A1 | 9/2010 | Pan |
| 2010/0239512 A1 | 9/2010 | Morris et al. |
| 2010/0247611 A1 | 9/2010 | Balkus, Jr. et al. |
| 2010/0247680 A1 | 9/2010 | Szabo |
| 2010/0255062 A1 | 10/2010 | Kalivretenos et al. |
| 2010/0256755 A1 | 10/2010 | Chen et al. |
| 2010/0261930 A1 | 10/2010 | Honda et al. |
| 2010/0262238 A1 | 10/2010 | Chen et al. |
| 2010/0268149 A1 | 10/2010 | Av-Gay et al. |
| 2010/0276284 A1 | 11/2010 | Meyerhoff et al. |
| 2010/0280122 A1 | 11/2010 | Fossel |
| 2010/0285100 A1 | 11/2010 | Balkus, Jr. et al. |
| 2010/0303891 A1 | 12/2010 | Lee et al. |
| 2010/0311780 A1 | 12/2010 | Farber |
| 2010/0323036 A1 | 12/2010 | Fine |
| 2010/0324107 A1 | 12/2010 | Dos Santos et al. |
| 2010/0330582 A1* | 12/2010 | Nakamura ............... 435/7.1 |
| 2010/0331542 A1 | 12/2010 | Smith |
| 2010/0331968 A1 | 12/2010 | Morris et al. |
| 2011/0008815 A1 | 1/2011 | Stamler et al. |
| 2011/0033437 A1 | 2/2011 | Smith et al. |
| 2011/0046182 A1 | 2/2011 | Gilmer et al. |
| 2011/0059036 A1 | 3/2011 | Arnold et al. |
| 2011/0059189 A1 | 3/2011 | Cisneros |
| 2011/0065783 A1 | 3/2011 | O'Donnell et al. |
| 2011/0070318 A1 | 3/2011 | Jezek et al. |
| 2011/0071168 A1 | 3/2011 | Chopp et al. |
| 2011/0076313 A1 | 3/2011 | Av-Gay et al. |
| 2011/0104240 A1 | 5/2011 | Jones et al. |
| 2011/0106000 A1 | 5/2011 | Jones et al. |

FOREIGN PATENT DOCUMENTS

| | | |
|---|---|---|
| EP | 0 724 436 B1 | 7/2004 |
| EP | 1 411 908 B1 | 5/2005 |
| EP | 1 163 528 B1 | 11/2005 |
| EP | 1 681 068 A1 | 7/2006 |
| EP | 1 690 532 A1 | 8/2006 |
| EP | 1 690 554 A1 | 8/2006 |
| EP | 1 690 557 A1 | 8/2006 |
| EP | 1 690 558 A1 | 8/2006 |
| EP | 1 700 611 A1 | 9/2006 |
| EP | 1 704 876 A1 | 9/2006 |
| EP | 1 704 877 A1 | 9/2006 |
| EP | 1 704 879 A1 | 9/2006 |
| EP | 1 707 224 A1 | 10/2006 |
| EP | 1 728 438 A1 | 12/2006 |
| EP | 1 731 176 A1 | 12/2006 |
| EP | 1 757 278 A1 | 2/2007 |
| EP | 1 764 119 A1 | 3/2007 |
| EP | 1 790 335 A1 | 5/2007 |
| EP | 1 861 130 B1 | 9/2008 |
| EP | 1 343 547 B1 | 4/2009 |
| EP | 1 871 433 B1 | 4/2009 |
| EP | 1 161 248 B1 | 5/2009 |
| EP | 1 846 058 B1 | 7/2009 |
| EP | 2 233 437 A1 | 9/2010 |
| WO | WO 95/07691 A1 | 3/1995 |
| WO | WO 95/10267 A1 | 4/1995 |
| WO | WO 95/12394 A1 | 5/1995 |
| WO | WO 95/19767 A1 | 7/1995 |
| WO | WO 95/22335 A1 | 8/1995 |
| WO | WO 95/32715 A1 | 12/1995 |
| WO | WO 96/08966 A1 | 3/1996 |
| WO | WO 96/13164 A1 | 5/1996 |
| WO | WO 96/14844 A1 | 5/1996 |
| WO | WO 96/015781 A1 | 5/1996 |
| WO | WO 96/15797 A1 | 5/1996 |
| WO | WO 96/27386 A1 | 9/1996 |
| WO | WO 96/32118 A1 | 10/1996 |
| WO | WO 96/32136 A1 | 10/1996 |
| WO | WO 96/033757 A1 | 10/1996 |
| WO | WO 96/35416 A1 | 11/1996 |
| WO | WO 97/16983 A1 | 5/1997 |
| WO | WO 97/31654 A1 | 9/1997 |
| WO | WO 97/34014 A1 | 9/1997 |
| WO | WO 97/047254 A1 | 12/1997 |
| WO | WO 98/05689 A1 | 2/1998 |
| WO | WO 98/06389 A1 | 2/1998 |
| WO | WO 98/08482 A2 | 3/1998 |
| WO | WO 98/08482 A3 | 3/1998 |
| WO | WO 98/08496 A1 | 3/1998 |
| WO | WO 98/13358 A1 | 4/1998 |
| WO | WO 98/19996 A1 | 5/1998 |
| WO | WO 98/20015 A1 | 5/1998 |
| WO | WO 98/22090 A1 | 5/1998 |
| WO | WO 98/29101 A1 | 7/1998 |
| WO | WO 98/42661 A1 | 10/1998 |
| WO | WO 99/00070 A1 | 1/1999 |
| WO | WO 99/01427 A2 | 1/1999 |
| WO | WO 99/18949 A1 | 4/1999 |
| WO | WO 99/22729 A1 | 5/1999 |
| WO | WO 99/33823 A1 | 7/1999 |
| WO | WO 99/37616 A1 | 7/1999 |
| WO | WO 99/44595 A2 | 9/1999 |
| WO | WO 99/44595 A3 | 9/1999 |
| WO | WO 99/51221 A1 | 10/1999 |
| WO | WO 99/67210 A1 | 12/1999 |
| WO | WO 99/67296 A1 | 12/1999 |
| WO | WO 00/03640 A1 | 1/2000 |
| WO | WO 00/06151 A1 | 2/2000 |
| WO | WO 00/30658 A1 | 6/2000 |
| WO | WO 00/33877 A1 | 6/2000 |
| WO | WO 00/56333 A1 | 9/2000 |
| WO | WO 00/59304 A1 | 10/2000 |
| WO | WO 00/63462 | 10/2000 |
| WO | WO 00/76318 A1 | 12/2000 |
| WO | WO 01/12067 A1 | 2/2001 |
| WO | WO 01/15738 A2 | 3/2001 |
| WO | WO 01/15738 A3 | 3/2001 |
| WO | WO 01/26702 A2 | 4/2001 |
| WO | WO 01/26702 A3 | 4/2001 |
| WO | WO 01/45732 A2 | 6/2001 |
| WO | WO 01/45732 A3 | 6/2001 |
| WO | WO 01/70199 A1 | 9/2001 |
| WO | WO 01/85227 A2 | 11/2001 |
| WO | WO 01/85227 A3 | 11/2001 |
| WO | WO 01/89572 A1 | 11/2001 |
| WO | WO 02/17880 A2 | 3/2002 |
| WO | WO 02/17880 A3 | 3/2002 |

(56) References Cited

FOREIGN PATENT DOCUMENTS

| | | |
|---|---|---|
| WO | WO 02/017881 A2 | 3/2002 |
| WO | WO 02/017881 A3 | 3/2002 |
| WO | WO 02/20026 A2 | 3/2002 |
| WO | WO 02/20026 A3 | 3/2002 |
| WO | WO 02/32418 A1 | 4/2002 |
| WO | WO 02/34705 A2 | 5/2002 |
| WO | WO 02/43786 A2 | 6/2002 |
| WO | WO 02/43786 A3 | 6/2002 |
| WO | WO 02/47675 A1 | 6/2002 |
| WO | WO 02/051353 A2 | 7/2002 |
| WO | WO 02/051353 A3 | 7/2002 |
| WO | WO 02/056864 A2 | 7/2002 |
| WO | WO 02/056864 A3 | 7/2002 |
| WO | WO 02/056874 A2 | 7/2002 |
| WO | WO 02/056904 A1 | 7/2002 |
| WO | WO 02/070496 A1 | 9/2002 |
| WO | WO 02/076395 A2 | 10/2002 |
| WO | WO 02/076395 A3 | 10/2002 |
| WO | WO 03/004097 A1 | 1/2003 |
| WO | WO 03/006427 A1 | 1/2003 |
| WO | WO 03/015605 A2 | 2/2003 |
| WO | WO 03/015605 A3 | 2/2003 |
| WO | WO 03/017989 A1 | 3/2003 |
| WO | WO 03/026717 A1 | 4/2003 |
| WO | WO 03/030659 A1 | 4/2003 |
| WO | WO 03/041713 A1 | 5/2003 |
| WO | WO 03/047636 A2 | 6/2003 |
| WO | WO 03/047636 A3 | 6/2003 |
| WO | WO 03/080039 A1 | 10/2003 |
| WO | WO 03/092763 A1 | 11/2003 |
| WO | WO 03/095398 A2 | 11/2003 |
| WO | WO 03/095398 A3 | 11/2003 |
| WO | WO 2004/009066 A1 | 1/2004 |
| WO | WO 2004/009253 A1 | 1/2004 |
| WO | WO 2004/011421 A1 | 2/2004 |
| WO | WO 2004/012874 A1 | 2/2004 |
| WO | WO 2004/037798 A1 | 5/2004 |
| WO | WO 2004/039313 A2 | 5/2004 |
| WO | WO 2004/039313 A3 | 5/2004 |
| WO | WO 2004/060283 A2 | 7/2004 |
| WO | WO 2004/064767 A2 | 8/2004 |
| WO | WO 2004/064767 A3 | 8/2004 |
| WO | WO 2004/087212 A2 | 10/2004 |
| WO | WO 2004/098538 A2 | 11/2004 |
| WO | WO 2004/098538 A3 | 11/2004 |
| WO | WO 2005/003032 A1 | 1/2005 |
| WO | WO 2005/011575 A2 | 2/2005 |
| WO | WO 2005/011575 A3 | 2/2005 |
| WO | WO 2005/030118 A2 | 4/2005 |
| WO | WO 2005/030118 A3 | 4/2005 |
| WO | WO 2005/030135 A2 | 4/2005 |
| WO | WO 2005/030135 A3 | 4/2005 |
| WO | WO 2005/030147 A2 | 4/2005 |
| WO | WO 2005/030147 A3 | 4/2005 |
| WO | WO 2005/034860 A2 | 4/2005 |
| WO | WO 2005/034860 A3 | 4/2005 |
| WO | WO 2005/039664 A2 | 5/2005 |
| WO | WO 2005/039664 A3 | 5/2005 |
| WO | WO 2005/067986 A1 | 7/2005 |
| WO | WO 2005/070006 A2 | 8/2005 |
| WO | WO 2005/070006 A3 | 8/2005 |
| WO | WO 2005/070008 A2 | 8/2005 |
| WO | WO 2005/070008 A3 | 8/2005 |
| WO | WO 2005/070874 A1 | 8/2005 |
| WO | WO 2005/070883 A1 | 8/2005 |
| WO | WO 2005/072819 A1 | 8/2005 |
| WO | WO 2005/077962 A2 | 8/2005 |
| WO | WO 2005/077962 A3 | 8/2005 |
| WO | WO 2005/081752 A2 | 9/2005 |
| WO | WO 2005/081752 A3 | 9/2005 |
| WO | WO 2005/081964 A2 | 9/2005 |
| WO | WO 2005/094913 A1 | 10/2005 |
| WO | WO 2005/102282 A1 | 11/2005 |
| WO | WO 2005/107384 A2 | 11/2005 |
| WO | WO 2005/107384 A3 | 11/2005 |
| WO | WO 2005/112954 A1 | 12/2005 |
| WO | WO 2005/115440 A2 | 12/2005 |
| WO | WO 2005/115440 A3 | 12/2005 |
| WO | WO 2005/120493 A1 | 12/2005 |
| WO | WO 2006/023693 A2 | 3/2006 |
| WO | WO 2006/023693 A3 | 3/2006 |
| WO | WO 2006/037105 A2 | 4/2006 |
| WO | WO 2006/037105 A3 | 4/2006 |
| WO | WO 2006/041855 A2 | 4/2006 |
| WO | wo 2006/041855 A3 | 4/2006 |
| WO | WO 2006/045639 A1 | 5/2006 |
| WO | WO 2006/055542 A2 | 5/2006 |
| WO | WO 2006/055542 A3 | 5/2006 |
| WO | WO 2006/058318 A2 | 6/2006 |
| WO | WO 2006/064056 A2 | 6/2006 |
| WO | WO 2006/066362 A1 | 6/2006 |
| WO | WO 2006/084909 A1 | 8/2006 |
| WO | WO 2006/084910 A2 | 8/2006 |
| WO | WO 2006/084911 A2 | 8/2006 |
| WO | WO 2006/084912 A1 | 8/2006 |
| WO | WO 2006/084913 A2 | 8/2006 |
| WO | WO 2006/084914 A2 | 8/2006 |
| WO | WO 2006/095193 A2 | 9/2006 |
| WO | WO 2006/095193 A3 | 9/2006 |
| WO | WO 2006/096572 A1 | 9/2006 |
| WO | WO 2006/097348 A1 | 9/2006 |
| WO | WO 2006/099058 A2 | 9/2006 |
| WO | WO 2006/099058 A3 | 9/2006 |
| WO | WO 2006/100154 A1 | 9/2006 |
| WO | WO 2006/100155 A1 | 9/2006 |
| WO | WO 2006/100156 A2 | 9/2006 |
| WO | WO 2006/122960 A1 | 11/2006 |
| WO | WO 2006/122961 A1 | 11/2006 |
| WO | WO 2006/125016 A1 | 11/2006 |
| WO | WO 2006/125262 A1 | 11/2006 |
| WO | WO 2006/127591 A2 | 11/2006 |
| WO | WO 2006/127591 A3 | 11/2006 |
| WO | WO 2006/128121 A2 | 11/2006 |
| WO | WO 2006/128742 A2 | 12/2006 |
| WO | WO 2006/128742 A3 | 12/2006 |
| WO | WO 2006/128743 A1 | 12/2006 |
| WO | WO 2006/130982 A1 | 12/2006 |
| WO | WO 2007/003028 A1 | 1/2007 |
| WO | WO 2007/005910 A2 | 1/2007 |
| WO | WO 2007/005910 A3 | 1/2007 |
| WO | WO 2007/012165 A1 | 2/2007 |
| WO | WO 2007/016677 A2 | 2/2007 |
| WO | WO 2007/016677 A3 | 2/2007 |
| WO | WO 2007/023005 A1 | 3/2007 |
| WO | WO 2007/024501 A2 | 3/2007 |
| WO | WO 2007/024501 A3 | 3/2007 |
| WO | WO 2007/027859 A1 | 3/2007 |
| WO | WO 2007/028657 A1 | 3/2007 |
| WO | WO 2007/030266 A2 | 3/2007 |
| WO | WO 2007/030266 A3 | 3/2007 |
| WO | WO 2007/050379 A2 | 5/2007 |
| WO | WO 2007/050379 A3 | 5/2007 |
| WO | WO 2007/053292 A2 | 5/2007 |
| WO | WO 2007/053578 A2 | 5/2007 |
| WO | WO 2007/053578 A3 | 5/2007 |
| WO | WO 2007/054373 A1 | 5/2007 |
| WO | wo 2007/057763 A2 | 5/2007 |
| WO | WO 2007/057763 A3 | 5/2007 |
| WO | WO 2007/059311 A2 | 5/2007 |
| WO | WO 2007/059311 A3 | 5/2007 |
| WO | WO 2007/064895 A2 | 6/2007 |
| WO | WO 2007/064895 A3 | 6/2007 |
| WO | WO 2007/067477 A1 | 6/2007 |
| WO | WO 2007/084533 A2 | 7/2007 |
| WO | WO 2007/084533 A3 | 7/2007 |
| WO | WO 2007/086884 A2 | 8/2007 |
| WO | WO 2007/086884 A3 | 8/2007 |
| WO | WO 2007/088050 A2 | 8/2007 |
| WO | WO 2007/088050 A3 | 8/2007 |
| WO | WO 2007/088123 A2 | 8/2007 |
| WO | WO 2007/088123 A3 | 8/2007 |
| WO | WO 2007/092284 A2 | 8/2007 |
| WO | WO 2007/092284 A3 | 8/2007 |
| WO | WO 2007/100910 A2 | 9/2007 |

(56) References Cited

FOREIGN PATENT DOCUMENTS

| | | |
|---|---|---|
| WO | WO 2007/100910 A3 | 9/2007 |
| WO | WO 2007/103190 A2 | 9/2007 |
| WO | WO 2007/103190 A3 | 9/2007 |
| WO | WO 2007/127725 A2 | 11/2007 |
| WO | WO 2007/127725 A3 | 11/2007 |
| WO | WO 2007/133922 A2 | 11/2007 |
| WO | WO 2007/133922 A3 | 11/2007 |
| WO | WO 2007/143185 A2 | 12/2007 |
| WO | WO 2007/143185 A3 | 12/2007 |
| WO | WO 2007/149437 A1 | 12/2007 |
| WO | WO 2007/149520 A2 | 12/2007 |
| WO | WO 2007/149520 A3 | 12/2007 |
| WO | WO 2008/005313 A2 | 1/2008 |
| WO | WO 2008/005313 A3 | 1/2008 |
| WO | WO 2008/013633 A2 | 1/2008 |
| WO | WO 2008/013633 A3 | 1/2008 |
| WO | WO 2008/020218 A1 | 2/2008 |
| WO | WO 2008/027203 A2 | 3/2008 |
| WO | WO 2008/027203 A3 | 3/2008 |
| WO | WO 2008/062160 A1 | 5/2008 |
| WO | WO 2008/071242 A1 | 6/2008 |
| WO | WO 2008/088507 A2 | 7/2008 |
| WO | WO 2008/088507 A3 | 7/2008 |
| WO | WO 2008/095841 A2 | 8/2008 |
| WO | WO 2008/095841 A3 | 8/2008 |
| WO | WO 2008/098192 A2 | 8/2008 |
| WO | WO 2008/098192 A3 | 8/2008 |
| WO | WO 2008/100591 A2 | 8/2008 |
| WO | WO 2008/100591 A3 | 8/2008 |
| WO | WO 2008/112391 A2 | 9/2008 |
| WO | WO 2008/112391 A3 | 9/2008 |
| WO | WO 2008/116497 A1 | 10/2008 |
| WO | WO 2008/116925 A1 | 10/2008 |
| WO | WO 2008/130567 A1 | 10/2008 |
| WO | WO 2008/141416 A1 | 11/2008 |
| WO | WO 2008/150505 A1 | 12/2008 |
| WO | WO 2008/157393 A1 | 12/2008 |
| WO | WO 2009/014616 A1 | 1/2009 |
| WO | WO 2009/014829 A2 | 1/2009 |
| WO | WO 2009/014829 A3 | 1/2009 |
| WO | WO 2009/019498 A2 | 2/2009 |
| WO | WO 2009/019498 A3 | 2/2009 |
| WO | WO 2009/019499 A2 | 2/2009 |
| WO | WO 2009/026680 A1 | 3/2009 |
| WO | WO 2009/036571 A1 | 3/2009 |
| WO | WO 2009/049208 A1 | 4/2009 |
| WO | WO 2009/064861 A2 | 5/2009 |
| WO | WO 2009/064861 A3 | 5/2009 |
| WO | WO 2009/073643 A2 | 6/2009 |
| WO | WO 2009/073643 A3 | 6/2009 |
| WO | WO 2009/073940 A2 | 6/2009 |
| WO | WO 2009/073940 A3 | 6/2009 |
| WO | WO 2009/080795 A1 | 7/2009 |
| WO | WO 2009/086470 A2 | 7/2009 |
| WO | WO 2009/086470 A3 | 7/2009 |
| WO | WO 2009/088433 A1 | 7/2009 |
| WO | WO 2009/098113 A1 | 8/2009 |
| WO | WO 2009/117182 A2 | 9/2009 |
| WO | WO 2009/117182 A3 | 9/2009 |
| WO | WO 2009/117183 A1 | 9/2009 |
| WO | WO 2009/124379 A1 | 10/2009 |
| WO | WO 2009/131931 A1 | 10/2009 |
| WO | WO 2009/155689 A1 | 12/2009 |
| WO | WO 2009/155690 A1 | 12/2009 |
| WO | WO 2010/002450 A2 | 1/2010 |
| WO | WO 2010/002450 A3 | 1/2010 |
| WO | WO 2010/033242 A2 | 3/2010 |
| WO | WO 2010/033242 A3 | 3/2010 |
| WO | WO 2010/045465 A1 | 4/2010 |
| WO | WO 2010/048724 A1 | 5/2010 |
| WO | WO 2010/080213 A2 | 7/2010 |
| WO | WO 2010/080213 A3 | 7/2010 |
| WO | WO 2010/096320 A2 | 8/2010 |
| WO | WO 2010/096320 A3 | 8/2010 |
| WO | WO 2010/114669 A1 | 10/2010 |
| WO | WO 2010/120414 A2 | 10/2010 |
| WO | WO 2010/151505 A1 | 12/2010 |
| WO | WO 2012/118819 A2 | 9/2012 |

OTHER PUBLICATIONS

Al-Sa'Doni et al., "S-Nitrosothiols as Nitric Oxide-Donors: Chemistry, Biology and Possible Future Therapeutic Applications", *Current Medicinal Chemistry*, 2004, 11: 2679-2690.

Al-Sa'Doni et al., "Current Status and Future Possibilities of Nitric Oxide-Donor Drugs: Focus on S-Nitrosothiols", *Mini-Reviews in Medicinal Chemistry*, 2005, 5: 247-254.

Albert, Klaus, "NMR investigations of stationary phases", *Journal of Separation Science*, 2003, 26: 215-224.

Bainbrigge et al., "The thermal stability of S-nitrosothiols: experimental studies andab initio calculations on model compounds", *Journal of the Chemical Society, Perkin Transactions*, 1997, 2: 351-353.

Bartberger et al., "Theory, Spectroscopy, and Crystallographic Analysis of S-Nitrosothiols: Conformational Distribution Dictates Spectroscopic Behavior", *Journal of the American Chemical Society*, 2000, 122: 5889-5890.

Bogush et al., "Preparation of Monodisperse Silica Particles: Control of Size and Mass Fraction", *Journal of Non-Crystalline Solids*, 1988, 104: 95-106.

Branda et al., "The effect of mixing alkoxides on the Stober particles size", *Colloids and Surfaces A: Physicochemical and Engineering Aspects*, 2007, 299: 252-255.

Brinker et al., *Sol-Gel Science: The Physics and Chemistry of Sol-Gel Processing*, Chapter 3, "Hydrolysis and Condensation II: Silicates", pp. 97-234, 1990.

Brinker et al., *Sol-Gel Science: The Physics and Chemistry of Sol-Gel Processing*, Chapter 4, "Particulate Sols and Gels", pp. 235-302, 1990.

Brinker et al., *Sol-Gel Science: The Physics and Chemistry of Sol-Gel Processing*, Chapter 8, "Drying", pp. 453-514, 1990.

Brinker et al., *Sol-Gel Science: The Physics and Chemistry of Sol-Gel Processing*, Chapter 9, "Structural Evolution During Consolidation", pp. 515-616, 1990.

Brinker et al., *Sol-Gel Science: The Physics and Chemistry of Sol-Gel Processing*, Chapter 10, "Surface Chemistry and Chemical Modification", pp. 617-674, 1990.

Brinker et al., *Sol-Gel Science: The Physics and Chemistry of Sol-Gel Processing*, Chapter 13, "Film Formation", pp. 787-838, 1990.

Brunner et al., "In Vitro Cytotoxicity of Oxide Nanoparticles: Comparison to Asbestos, Silica, and the Effect of Particle Solubility", *Environmental Science and Technology*, 2006, 40: 4374-4381.

Butler et al., "Chemistry, Analysis, and Biological Roles of S-Nitrosothiols", *Analytical Biochemistry*, 1997, 249: 1-9.

Cassidy et al., "Drug delivery strategies for photodynamic antimicrobial chemotherapy: From benchtop to clinical practice", *Journal Photochemistry and Photobiology B: Biology*, 2009, 95(2): 71-80, (Abstract Only).

Charville et al., "Reduced bacterial adhesion to fibrinogen-coated substrates via nitric oxide release", *Biomaterials*, 2008, 29(30): 4039-4044.

Coneski et al., "Degradable Nitric Oxide-Releasing Biomaterials via Post-Polymerization Functionalization of Cross-Linked Polyesters", *Biomacromolecules*, 2010, 11: 3208-3215.

Coneski et al., "Synthesis of nitric oxide-releasing polyurethanes with S-nitrosothiol-containing hard and soft segments", *Polymer Chemistry*, 2011, 2: 906-913.

Cooke, John, "NO and angiogenesis", *Atherosclerosis Supplements*, 2003, 4: 53-60.

Crichton et al., "Old Iron, Young Copper: from Mars to Venus", *BioMetals*, 2001, 14: 99-112.

De Souza et al., "Leishmanicidal activity of primary S-nitrosothiols against *Leishmania major* and *Leishmania amazonensis*: Implications for the treatment of cutaneous leishmaniasis", *Nitric Oxide*, 2006, 15: 209-216.

(56) References Cited

OTHER PUBLICATIONS

Deupree et al., "Morphological analysis of the antimicrobial action of nitric oxide on Gram-negative pathogens using atomic force microscopy", Acta Biomaterialia, 2009, 5:1405-1415.

Dicks et al., "Identification of $Cu^+$ as the effective reagent in nitric oxide formation from S-nitrosothiols (RSNO)", Journal of the Chemical Society, 1996, 2: 481-487.

Dobmeier et al., "Nitric Oxide-Releasing Xerogel-Based Fiber-Optic pH Sensors", Analytical Chemistry, 2006, 78: 7461-7466.

Etchenique et al., "Photodelivery of Nitric Oxide from a Nitrosothiol-Derivatized Surface", Journal of the American Chemical Society, 2000, 122: 3967-3968.

Foster et al., "Photocatalytic disinfection using titanium dioxide: spectrum and mechanism of antimicrobial activity", Applied Microbiology Biotechnology, 2011, 90(6): 1847-1868.

Frost et al., "Polymers incorporating nitric oxide releasing/generating substances for improved biocompatibility of blood-contacting medical devices", Biomaterials, 2005, 26(14): 1685-1695.

Garcia et al., "S-Nitroso-N-Acetylcysteine (SNAC) Prevents Myocardial Alterations in Hypercholesterolemic LDL Receptor Knockout Mice by Antiinflammatory Action", Journal of Cardiovascular Pharmacology and Therapeutics, 2008, 51: 78-85.

Gaslain et al., "One-step preparation of thiol-modified mesoporous silica spheres with various functionalization levels and different pore structures", Journal of Sol-Gel Science and Technology, 2009, 49: 112-124.

Grossi et al., "A Kinetic Study of S-Nitrosothiol Decomposition", Chemistry—A European Journal, 2002, 8(2): 380-387.

Hatton et al., "Past, Present, and Future of Periodic Mesoporous Organosilicas—The PMOs", Accounts of Chemical Research, 2005, 38: 305-312.

Hetrick et al., "Reducing implant-related infections: active release strategies", Chemical Society Reviews, 2006, 35: 780-789.

Hetrick et al., "Reduced foreign body response at nitric oxide-releasing subcutaneous implants", Biomaterials, 2007, 28(31): 4571-4580.

Hetrick et al., "Antibacterial nitric oxide-releasing xerogels: Cell viability and parallel plate flow cell adhesion studies", Biomaterials, 2007, 28(11): 1948-1956.

Hogg, Neil, "Biological Chemistry and Clinical Potential of S-Nitrosothiols", Free Radical Biology & Medicine, 2000, 28(10): 1478-1486.

Huang et al., "Synthesis of uniform, spherical sub-100 nm silica particles using a conceptual modification of the classic LaMer model", Colloids and Surfaces A: Physicochemical and Engineering Aspects, 2010, 360: 175-183.

International Preliminary Report on Patentability corresponding to International Application No. PCT/US2012/026960; mailed Mar. 13, 2014; 6 pages.

International Preliminary Report on Patentability corresponding to International Application No. PCT/US2012/026972; mailed Mar. 13, 2014; 6 pages.

Johnston et al., "Porous functionalised silica particles: a potential platform for biomolecular screening", Chemical Communications, 2005, p. 848-850.

Johnston et al., "A Mechanism for Forming Large Fluorescent Organo-Silica Particles: Potential Supports for Combinatorial Synthesis", Chemistry of Materials, 2006, 18: 6163-6169.

Katayama et al., "Design and Evaluation of S-Nitrosylated Human Serum Albumin as a Novel Anticancer Drug", The Journal of Pharmacology and Experimental Therapeutics, 2008, 325(1): 69-76.

Katsumi et al., "Physicochemical, Tissue Distribution, and Vasodilation Characteristics of Nitrosated Serum Albumin: Delivery of Nitric Oxide In Vivo", Journal of Pharmaceutical Sciences, 2004, 93(9): 2343-2352.

Katsumi et al., "Development of Polyethylene Glycol-Conjugated Poly-S-Nitrosated Serum Albumin, a Novel S-Nitrosothiol for Prolonged Delivery of Nitric Oxide in the Blood Circulation in Vivo", The Journal of Pharmacology and Experimental Therapeutics, 2005, 314(3): 1117-1124.

Kim et al., "Effect of electrolyte additives on sol-precipitated nano silica particles", Ceramics International, 2004, 30: 171-175.

Kim et al., "Size Control of Silica Nanoparticles and Their Surface Treatment for Fabrication of Dental Nanocomposites", Biomacromolecules, 2007, 8: 215-222.

Langford et al., "Inhibition of platelet activity by S-nitrosoglutathione during coronary angioplasty", The Lancet, 1994, 344: 1458-1460.

Laszlo et al., "Attenuation by nitrosothiol NO donors of acute intestinal microvascular dysfunction in the rat", British Journal of Pharmacology, 1995, 115: 498-502.

Lee et al., "Preparation of Highly Monodispersed Hybrid Silica Spheres Using a One-Step Sol-Gel Reaction in Aqueous Solution", Langmuir, 2007, 23(22): 10875-10878.

Lin et al., "Structural and Morphological Control of Cationic Surfactant-Templated Mesoporous Silica", Accounts of Chemical Research, 2002, 35: 927-935.

Lin et al., "Preparation of functionalized tertiary thiols and nitrosothiols", Tetrahedron, 2006, 62(35): 8410-8418.

Marxer et al., "Preparation of Nitric Oxide (NO)-Releasing Sol-Gels for Biomaterial Application", Chemistry of Materials, 2003, 15: 4193-4199.

Marxer et al., "Sol-gel derived nitric oxide-releasing oxygen sensors", Analyst, 2005, 130: 206-212.

Meng et al., "Preparation of Highly Monodisperse Hybrid Silica Nanospheres Using a One-Step Emulsion Reaction in Aqueous Solution", Langmuir, 2009, 25(14): 7879-7883.

Miller et al., "Functionalized Organosilica Microspheres via a Novel Emulsion-Based Route", Langmuir, 2005, 21: 9733-9740.

Mocellin et al., "Nitric Oxide, a Double Edged Sword in Cancer Biology: Searching for Therapeutic Opportunities", Medicinal Research Reviews, 2007, 27: 317-352.

Mosquera et al., "New route for producing crack-free xerogels: Obtaining uniform pore size", Journal of Non-Crystalline Solids, 2008, 354: 645-650.

Mowery et al., "Preparation and characterization of hydrophobic polymeric films that are thromboresistant via nitric oxide release", Biomaterials, 2000, 21: 9-21.

Nablo et al., "Sol-Gel Derived Nitric-Oxide Releasing Materials that Reduce Bacterial Adhesion", Journal of the American Chemical Society, 2001, 123: 9712-9713.

Nablo et al., "Antibacterial properties of nitric oxide-releasing sol-gels", Journal of Biomedical Materials Research Part A, 2003, 67A: 1276-1283.

Nablo et al., "Poly(vinyl chloride)-Coated Sol-Gels for Studying the Effects of Nitric Oxide Release on Bacterial Adhesion", Biomacromolecules, 2004, 5: 2034-2041.

Nablo et al., "Inhibition of implant-associated infections via nitric oxide release", Biomaterials, 2005, 26(34): 6984-6990.

Nablo et al., "Nitric oxide-releasing sol-gels as antibacterial coatings for orthopedic implants", Biomaterials, 2005, 26: 917-924.

Nakamura et al., "Synthesis and Characterization of Organosilica Nanoparticles Prepared from 3-Mercaptopropyltrimethoxysilane as the Single Silica Source", The Journal of Physical Chemistry C, 2007, 111: 18892-18898.

Nakamura et al., "One-Pot Synthesis and Characterization of Three Kinds of Thiol-Organosilica Nanoparticles", Langmuir, 2008, 24: 5099-5108.

Noimark et al., "The role of surfaces in catheter-associated infections", Chemical Society Reviews, 2009, 38: 3435-3448.

O'Halloran et al., "Metallochaperones, an Intracellular Shuttle Service for Metal Ions", The Journal of Biological Chemistry, 2000, 275(33): 25057-25060.

Osterholtz et al., "Kinetics of the hydrolysis and condensation of organofunctional alkoxysilanes: a review", Journal of Adhesion Science and Technology, 1992, 6(1): 127-149.

(56) References Cited

OTHER PUBLICATIONS

Page et al., "Antimicrobial surfaces and their potential in reducing the role of the inanimate environment in the incidence of hospital-acquired infections", *Journal Materials Chemistry—The Royal Society of Chemistry*, 2009, 19: 3819-3831.
Park et al., "Preparation of silica nanoparticles: determination of the optimal synthesis conditions for small and uniform particles", *Colloids and Surfaces A: Physicochemical and Engineering Aspects*, 2002, 197: 7-17.
Pavlos et al., "Photosensitive precursors to nitric oxide", *Current Topics in Medicinal Chemistry*, 2005, 5: 635-645.
Polizzi et al., "Water-Soluble Nitric Oxide-Releasing Gold Nanoparticles", *Langmuir*, 2007, 23: 4938-4943.
Privett et al., "Efficacy of surface-generated nitric oxide against Candida albicans adhesion and biofilm formation", *Biofouling*, 2010, 26(8): 973-983.
Radomski et al., "S-nitroso-glutathione inhibits platelet activation in vitro and in vivo", *British Journal of Pharmacology*, 1992, 107: 745-749.
Rahman et al., "An optimized sol-gel synthesis of stable primary equivalent silica particles", *Colloids and Surfaces A: Physicochemical and Engineering Aspects*, 2007, 294: 102-110.
Ramsay et al., "Systemic effects of S-nitroso-glutathione in the human following intravenous infusion", *British Journal of Clinical Pharmacology*, 1995, 40: 101-102.
Rao et al., "Synthesis of flexible silica aerogels using methyltrimethoxysilane (MTMS) precursor", *Journal Colloid Interface Science*, 2006, 300: 279-285.
Reynolds et al., "Nitric Oxide-Releasing Hydrophobic Polymers: Preparation, Characterization, and Potential Biomedical Applications", *Free Radical Biology & Medicine*, 2004, 37(7): 926-936.
Riccio et al., "Stöber Synthesis of Nitric Oxide-Releasing S-Nitrosothiol-Modified Silica Particles", *Chemistry of Materials*, 2011, 23: 1727-1735.
Richardson et al., "Potential therapeutic uses for S-nitrosothiols", *Clinical Science*, 2002, 102: 99-105.
Rojas et al., "Polyurethane coating release bioactive antibodies to reduce bacterial adhesion", *Journal of Controlled Release*, 2000, 63: 175-189.
Sakka et al., "Formation of sheets and coating films from alkoxide solutions", *Journal Non-Crystalline Solids*, 1984, 63(1-2): 223-235.
Scherer, George, "Effect of Shrinkage on the Modulus of Silica Gel", *Journal of Non-Crystalline Solids*, 1989, 109: 183-190.
Schmidt, H., "Organically Modified Silicates by the Sol-Gel Process", *Materials Research Society Symposia Proceedings*, 1984, 32: 327-335.
Schmidt et al., "Principles of hydrolysis and condensation of alkoxysilanes", *Journal Non-Crystalline Solids*, 1984, 63(1-2): 1-11.
Seabra et al., "Polynitrosated Polyesters: Preparation, Characterization, and Potential Use for Topical Nitric Oxide Release", *Biomacromolecules*, 2005, 6: 2512-2520.
Seabra et al., "Nitric oxide-releasing vehicles for biomedical applications", *Journal of Materials Chemistry*, 2009, 20: 1624-1637.
Seabra et al., "Antibacterial Nitric Oxide-Releasing Polyester for the Coating of Blood-Contacting Artificial Materials", *Artificial Organs*, 2010, 34(7): E204-E214.
Shin et al., "Inorganic/Organic Hybrid Silica Nanoparticles as a Nitric Oxide Delivery Scaffold", *Chemistry of Materials*, 2008, 20: 239-249.
Sinha et al., "UV-induced DNA damage and repair: a review", *Photochemical & Photobiological Sciences*, 2002, 1: 225-236.
Sortino et al., "Light-controlled nitric oxide delivering molecular assemblies", *Chemical Society Reviews*, 2010, 39: 2903-2913.
Stasko et al., "S-Nitrosothiol-Modified Dendrimers as Nitric Oxide Delivery Vehicles", *Biomacromolecules*, 2008, 9(3):834-841.
Stein et al., "Hybrid Inorganic-Organic Mesoporous Silicates—Nanoscopic Reactors Coming of Age", *Advanced Materials*, 2000, 12(19): 1403-1419.
Stober et al., "Controlled Growth of Monodisperse Silica Spheres in the Micron Size Range", *Journal of Colloid and Interface Science*, 1968, 26: 62-69.
Tan et al., "Study of the Effects of Progressive Changes in Alkoxysilane Structure on Sol-Gel Reactivity", *The Journal of Physical Chemistry B*, 2006, 110: 22353-22364.
Valko et al., "Metals, Toxicity and Oxidative Stress", *Current Medicinal Chemistry*, 2005, 12: 1161-1208.
Van Helden et al., "Preparation and Characterization of Spherical Monodisperse Silica Dispersions in Nonaqueous Solvents", *Journal of Colloid and Interface Science*, 1981, 81(2): 354-368.
Varu et al., "Basic Science Review: Nitric Oxide—Releasing Prosthetic Materials", *Vascular & Endovasc Surgery*, 2009, 43: 121-131.
Vogel et al., "Fluorescent organosilica micro- and nanoparticles with controllable size", *Journal of Colloid and Interface Science*, 2007, 310: 144-150.
Walcarius et al., "Rate of Access to the Binding Sites in Organically Modified Silicates. 3. Effect of Structure and Density of Functional Groups in Mesoporous Solids Obtained by the Co-Condensation Route", *Chemistry of Materials*, 2003, 15: 4181-4192.
Walshe et al., "Wilson's disease: the importance of measuring serum caeruloplasmin non-immunologically", *Annals of Clinical Biochemistry*, 2003, 40: 115-121.
Wang et al., "Nitric Oxide Donors: Chemical Activites and Biological Applications", *Chemical Reviews*, 2002, 102: 1091-1134.
Williams et al., "The Chemistry of S-Nitrosothials", *Accounts of Chemical Research*, 1999, 32: 869-876.
Williams et al., "A chemist's view of the nitric oxide story", *Organic & Biomolecular Chemistry*, 2003, 1: 441-449.
Yoo et al., "Influence of Reaction Parameters on Size and Shape of Silica Nanoparticles", *Journal of Nanoscience and Nanotechnology*, 2006, 6: 3343-3346.
Extended European Search Report corresponding to European Patent Application No. 12752627.5: 5 pages (mailed Jul. 2, 2015).
Barbe et al., "Silica Particles: A Novel Drug-Delivery System", *Advanced Materials*, 2004, 16(21): 1959-1965.
Dobmeier et al., "Antibacterial Properties of Nitric Oxide-Releasing Sol-Gel Microarrays", *Biomacromolecules*, 2004, 5: 2493-2495.
Farias-Eisner et al., "The Chemistry and Tumoricidal Activity of Nitric Oxide/Hydrogen Peroxide and the Implications to Cell Resistance/Susceptibility", *The Journal of Biological Chemistry*, 1996, 271(11): 6144-6151.
Pulfer et al., "Incorporation of nitric oxide-releasing crosslinked polyethyleneimine microspheres into vascular grafts", *Journal of Biomedical Materials Research*, 1997, 37(2): 182-189.
Shin et al., "Nitric Oxide-Releasing Sol-Gel Particle/Polyurethane Glucose Biosensors", *Analytical Chemistry*, 2004, 76: 4543-4549.
English Translation of Chinese Office Action Corresponding to Chinese Patent Application No. 201080056580.6; Date of Issue: Feb. 25, 2015 (14 pages).
Huang "The mechanism and technique of Sol-Gel" *Chemical Industry Press* 1st Edition: 15 pages (2005).
Amadeu et al., "Nitric Oxide Donor Improves Healing if Applied on Inflammatory and Proliferative Disease" *Journal of Surgical Research* 149: 84-93 (2008).
Ashutosh, K. et al., "Use of nitric oxide inhalationin chronic obstructive pulmonary disease" *Thorax* 55:109-113 (2000).
Azizzadeh, B. et al., "Nitric Oxide Improve Cisplatin Cytotoxicity in Head and Neck Squamous Cell Carcinoma" *Laryngoscope* 111:1896-1900 (2001).
Barst, R.J. et al., "Clinical perspectives with long-term pulsed inhaled nitric oxide for the treatment of pulmonary arterial hypertension" *Pulmonary Circulation* 2(2):139-147 (2012).
Barraud, N., et al., "Involvement of Nitric Oxide in Biofilm Dispersal of Pseudomonas aeruginosa" *Journal of Bacteriology* 188(21):7344-7353 (2006).
Benz S. et al., "Effect of Nitric Oxide in Ischemia/Reperfusion of the Pancreas" *Journal of Surgical Research* 106(1):46-53, (2002).
Bian K. et al., "Vascular System: Role of Nitric Oxide in Cardiovascular Diseases" *The Journal of Clinical Hypertension* 10(4):304-310 (2008).
Bloch K.D. et al. "Inhaled NO as a therapeutic agent" *Cardiovascular Research* 75:339-348 (2007).

(56) References Cited

OTHER PUBLICATIONS

Bohl Masters et al., "Effects of nitric oxide releasing vinyl poly(vinyl alcohol) hydrogel dressings on dermal wound healing in diabetic mice" *Wound Repair and Regeneration* 10(5): 286-294 (2002).
Bonavida B. et al., "Novel therapeutic applications of nitric oxide donors in cancer: Roles in chemo- and immunosensitization to apoptosis and inhibition of metastases" *Nitric Oxide* (19) 2:152-157 (2008).
Bonavida B. et al., "Therapeutic potential of nitric oxide in cancer" *rug Resistance Updates* 9(3):157-73 (2006).
Boykin J.V. et al., "HBO mediates increased nitric oxide production associated with wound healing", *Wound Repair and Regeneration* 12(2) (2004).
Boykin Jr. J.V., "Wound Nitric Oxide Bioactivity: A Promising Diagnostic Indicator for Diabetic Foot Ulcer Management", *Journal of Wound, Ostomy & Continence Nursing* 37(1):25-32 (2010).
Bruch-Gerharz D. et al., "Nitric Oxide in Human Skin: Current Status and Future Prospects", *Journal of Investigative Dermatology* 110:1-7 (1998).
Cals-Grierson M.M. et al., "Nitric oxide function in the skin", *Nitric Oxide* 10(4):179-193 (2004).
Carlsson S. et al., "Intravesical Nitric Oxide Delivery for Prevention of Catheter-Associated Urinary Tract Infections" *Antimicrobial Agents and Chemotherapy* 49(6):2352 (2005).
Coban, A., et al., "The Effect of Nitric Oxide Combined with Fluoroquinolones against Salmonellaenterica Serovar Typhimurium in Vitro," *Mem Inst Oswaldo Cruz*, Rio de Janeiro, 98(3):419-423 (2003).
De Groote M.A. et al., "NO Inhibitions: Antimicrobial Properties of Nitric Oxide", *Clinical Infectious Diseases* 21 (Supplement 2):S162-S165 (1995).
Fang F., "Mechanisms of Nitric Oxide-related Antimicrobial Activity" *Journal of Clinical Investigation* 99(12):2818-2825 (1997).
Frederiksen L.J. et al., "Chemosensitization of Cancer *In vitro* and *In vivo* by Nitric Oxide Signaling" *Clinical Cancer Research* 13:2199-2206 (2007).
Frost et al., "Controlled Photoinitiated Release of Nitric Oxide from Polymer Films Containing S-Nitroso-N-acetyle-DL-penicillamine Derivatized Fumed Silixa Filler" *Journal of the American Chemical Society* 2004, 126(5):1348-1349.
Frost et al., "Synthesis, characterization, and controlled nitric oxide release from S-nitrosothiol-derivatized fumed silica polymer filler particles" *Journal of Biomedical Research, Part A*, 72A:409-419 (2005).
Ghaffari A. et al., "Potential application of gaseous nitric oxide as a topical antimicrobial agent" *Nitric Oxide* 14(1):21-29 (2006).
Gupta, R., et al., "Bioactive materials for biomedical applications using sol-gel technology," *Biomedical Materials* 3:1-15 (2008).
Herman A.G. et al., "Therapeutic potential of nitric oxide donors in the prevention and treatment of atherosclerosis" *European Heart Journal* 26:1945-1955 (2005).
Hetrick E.M. et al., "Bactericidal Efficacy of Nitric Oxide-Releasing Silica Nanoparticles" *ACS Nano* 2(2):235-246 (2008).
Hetrick et al., "Anti-biofilm efficacy of nitric oxide-releasing silica nanoparticles", *Biomaterials* 30:2782-2789 (2009).
Hirst D. et al., "Targeting nitric oxide for cancer therapy", *Journal of Pharmacy and Pharmacology* 59:3-13 (2007).
Howlin R. et al., "Nitric oxide-mediated dispersal and enhanced antibiotic sensitivity in *pseudomonas aeruginosa* biofilms from the cystic fibrosis lung", *Archives of Disease in Childhood* 96:A45 (2011).
Hrabie et al., "Chemistry of the nitric oxide-releasing diazeniumdiolate ("nitrosohydroxylamine") functional group and its oxygen-substituted derivatives," *Chemical Reviews* 102:1135-1154 (2002).
Huerta S. et al., "Nitric oxide donors: Novel cancer therapeutics (Review)", *International Journal of Oncology* 33:909-927 (2008).

International Search Report and Written Opinion Corresponding to International Application No. PCT/US2012/26972; Date of Mailing: Feb. 28, 2012; 11 Pages.
International Search Report and Written Opinion Corresponding to International Application No. PCT/US2012/26960; Date of Mailing: Feb. 28, 2012; 18 Pages.
Iwakir, N. et al., Synthesis of Amphiphillic polysiloxanes and their properties for formation of nano-aggregates, *Colloid and Polymer Science* 287:577-582 (2009).
Johnson T. A. et al., "Reduced ischemia/reperfusion injury via glutathione-initiated nitric oxide-releasing dendrimers", *Nitric Oxide*, 2009, 7 Pages.
Jones M.L. et al., "Antimicrobial properties of nitric oxide and its application in antimicrobial formulations and medical devices", *Applied Microbiology and Biotechnology* 88:401-407 (2010).
Kiziltepe T. et al., "JS-K, a GST-activated nitric oxide generator, induces DNA double-strand breaks, activates DNA damage response pathways, and induces apoptosis in vitro and in vivo in human multiple myeloma cells", *Blood* 110:709-718 (2007).
Lamas S. et al., "Nitric oxide signaling comes of age: 20 years and thriving", *Cardiovascular Research* 75:207-209 (2007).
Liu X. et al., "Nitric Oxide Inhalation Improves Microvascular Flow and Decreases Infarction Size After Myocardial Ischemia and Reperfusion", *Journal of the American College of Cardiology*, vol. 50, No. 8 (2007).
Luo J. et al., "Nitric oxide: a newly discovered function on wound healing", *Acta Pharmacologica Sinica* 26(3):259-264 (2005).
McElhaney-Feser, G., et al., "Synergy of Nitric Oxide and Azoles against Candida Species In Vitro," *Antimicrobial Agents And Chemotherapy* 42(9):2342-2346 (1998).
McGrowder D. et al., "Therapeutic Uses of Nitric Oxide-donating Drugs in the Treatment of Cardiovascular Diseases" *International Journal of Pharmacology* 2(4): 366-373 (2006).
Napoli C. et al., "Nitric oxide and atherosclerosis: An update", *Nitric Oxide* 15(4):265-279 (2006).
Phillips L. et al., "Nitric Oxide Mechanism of Protection in Ischemia and Reperfusion Injury", *Journal of Investigative Surgery* 22:46-55 (2009).
Riccio et al., "Nitric oxide-releasing S-nitrosothiol-modified xerogels" *Biomaterials* 30:4494-4502 (2009).
Robson, MC, "Wound Infection. A Failure of Wound Healing Caused by an Imbalance of Bacteria," *Surgical Clinics of North America* 77(3): 637-50 (1997).
Rothrock A.R. et al., "Synthesis of Nitric Oxide-Releasing Gold Nanoparticles", *Journal of American Chemical Society* 127:9362-9363 (2005).
Saaral, NY, "The Equilibrium Between Endothelin-1/Nitric Oxide in Acne Vulgaris," *Istanbul Tip Fakultesi Dergisi Cilt*, 2008, 71(4).
Saavedra J.E. et al., "Esterase-Sensitive Nitric Oxide Donors of the Diazeniumdiolate Family: In Vitro Antileukemic Activity "*Journal of Medicinal Chemistry* 43:261-269 (2000).
Sato et al. "Dynamic Aspect of Reactive Oxygen and Nitric Oxide in Oral Cavity", *J. Clin. Biochem. Nutr.* 42:8-13 (2008).
Schäffer M.R. et al., "Diabetes-impaired healing and reduced wound nitric oxide synthesis: A possible pathophysiologic correlation", *Surgery* 121(5):513-519 (1997).
Schairer D.O. et al., "The potential of nitric oxide releasing therapies as antimicrobial agents" *Virulence* 3(3):271-279 (2012).
Schulz R. et al., "Nitric oxide in myocardial ischemia/reperfusion injury", *Cardiovascular Research* 61:402-413 (2004).
Schwentker A. et al., "Nitric oxide and wound repair: role of cytokines?" *Nitric Oxide* 7(1):1-10 (2002).
Shin et al. "Synthesis of Nitric Oxide-Releasing Silica Nanoparticles" *Journal of American Chemical Society* 129(15):4612-4619 (2007).
Shin et al. "Supporting Information: Synthesis of Nitric Oxide-Releasing Silica Nanoparticles" *Journal of American Chemical Society* 129(15):S1-S4 (2007).
Simeone A.M. et al., "N-(4-Hydroxyphenyl) retinamide and nitric oxide pro-drugs exhibit apoptotic and anti-invasive effects against bone metastatic breast cancer cells" *Carcinogenesis* 27(3):568-577 (2006).

(56) References Cited

OTHER PUBLICATIONS

Siriussawakul A. et al. "Role of nitric oxide in hepatic ischemia-reperfusion injury", *World Journal of Gastroenterology* 16(48): 6079-6086 (2010).
Shi, HP et al., "The role of iNOS in wound healing" *Surgery*, vol. 130(2):225-229 (2001).
Slowing et al. "Mesoporous silica nanoparticles as controlled release drug delivery and gene transfection carriers" *Advanced Drug Delivery Reviews* 60:1278-1288 (2008).
Stasko, N., et al., "Dendrimers as a Scaffold for Nitric Oxide Release," *J. Am. Chem. Soc.*, 2006, vol. 128, pp. 8265-8271.
Stevens E.V. et al., "Nitric Oxide-Releasing Silica Nanoparticle Inhibition of Ovarian Cancer Cell Growth", *Molecular Pharmaceutics* 7(3):775-785 (2010).
Summersgill, J., et al., "Killing of *Legionella pneumophila* by nitric oxide in γ-interferon-activated macrophages," *Journal of Leukocyte Biology* 52:625-629 (1992).
Tang, X., et al., "Synthesis of Beta-Lactamase Activated Nitric Oxide Donors," *Biorgania & Medicinal Chemistry Letters* 13:1687-1690 (2003).
Terpolilli N.A. et al., "Inhalation of Nitric Oxide Prevents Ischemic Brain Damage in Experimental Stroke by Selective Dilatation of Collateral Arterioles" *Circulation Research* 110:727-738 (2012).
Thomas D.D. et al., "Hypoxic inducible factor 1α, extracellular signal-regulated kinase, and p53 are regulated by distinct threshold concentrations of nitric oxide", *Proceedings of the National Academy of Sciences* 101(24):8894-8899 (2004).
Weller R. "Nitric oxide donors and the skin: useful therapeutic agents?" *Clinical Science* 105:533-535 (2003).
Wink D.A. et al., "The multifaceted roles of nitric oxide in cancer", *Carcinogenesis* 19(5):711-721 (1998).
Witte M.B. et al., "Nitric oxide enhances experimental wound healing in diabetes", *British Journal of Surgery* 89:1594-1601 (2002).
Witte M.B. et al., "Role of nitric oxide in wound repair", *The American Journal of Surgery* 183(4):406-412 (2002).
Yetik-Anacak G. et al., "Nitric oxide and the endothelium: History and impact on cardiovascular disease", *Vascular Pharmacology* 45(5):268-276 (2006).
Zhang H. et al., "Nitric Oxide-Releasing Fumed Silica Particles: Synthesis, Characterization, and Biomedical Application", *Journal of the American Chemical Society* 125:5015-5024 (2003).
Zhu, D., et al., "Corrosion protection of metals by water-based silane mixtures of bis-[trimethosysilylpropyl]amine and vinyltriacetoxysilane," *Progress in Organic Coatings* 49:42-53 (2004).
Zhu H. et al., "Effects of Nitric Oxide on Skin Burn Wound Healing", *Journal of Burn Care & Research* 29(5):804-814 (2008).
Zhu H. et al., "Nitric Oxide Accelerates the Recovery from Burn Wounds", *World Journal of Surgery* 31: 624-631 (2007).
European Search Report Corresponding to European Patent Application No. 09820905.9; Dated: Feb. 14, 2013; 7 Pages.
Living Water Acid-Alkaline Balance http://www.livingwaterhealthsolutions.com/Articles/alkalize.php Accessed online Nov. 3, 2011.
Salivary pH Testing https://allicincenter.com/pdf/ph_testing.pdf Accessed online Nov. 3, 2011.

\* cited by examiner

NITRIC OXIDE-RELEASING S-NITROSOTHIOL-MODIFIED SILICA PARTICLES AND METHODS OF MAKING THE SAME

CROSS-REFERENCE TO RELATED APPLICATIONS

This application is a continuation under 35 U.S.C. §111(a) of PCT Application No. PCT/US2012/026960, filed on Feb. 28, 2012, which claims the benefit, under 35 U.S.C. §119, of U.S. Provisional Application Ser. No. 61/447,368, filed Feb. 28, 2011, and U.S. Provisional Application No. 61/565,694, filed Dec. 1, 2011, the disclosure of each of which is hereby incorporated by reference herein in its entirety.

STATEMENT OF GOVERNMENT SUPPORT

The present invention was funded in part by government support under grant number 5-R01-EB000708 from the National Institutes of Health. The United States Government has certain rights in this invention.

FIELD OF THE INVENTION

The present invention relates to nitric oxide-releasing particles. More particularly, the present application relates to S-nitrosothiol-modified silica particles.

BACKGROUND OF THE INVENTION

Since the discovery of the physiological roles of nitric oxide (NO), much research has focused on the synthesis of NO-releasing materials/vehicles to elicit NO's characteristics as an antimicrobial agent, mediator of wound repair, or angiogenic cofactor. S-Nitrosothiols (RSNOs) are one class of endogenous NO donor believed to store/transport the majority of the body's natural reservoir of NO. As such, a large body of work has utilized low molecular weight RSNOs (e.g., S-nitroso-glutathione (GSNO), S-nitroso-N-acetylcysteine (SNAC), and S-nitroso-N-acetyl-penicillamine (SNAP)) as donors to spontaneously release NO. Although promising, the clinical application of low molecular weight NO donors has been slow due to both lack of tissue specific targeting and uncontrollable NO release kinetics. To address such shortcomings, NO donor precursors have been conjugated to larger scaffolds (e.g., proteins, dendrimers, and nanoparticles), thus enabling high NO storage per delivery vehicle and release profiles similar to their small molecule analogues.

Silica particles are among the most widely employed macromolecular scaffolds for biomedical applications due to facile synthetic strategies and minimal cytotoxicity. Previously, the surface of fumed silica particles (7-10 nm diameter) have been grafted with SNAP, SNAC, and S-nitrosocysteine (CysNO) to create S-nitrosothiol-modified silica particles. However, the NO storage was limited to 0.021-0.138 µmol mg$^{-1}$ because the thiol functionalization was restricted to the exterior of the particle. Additionally, these systems are not able to tune particle size to fit a therapeutic system of interest. Alternatively, the hydrolysis and co-condensation of organosilane and tetraalkoxysilane precursors via sol-gel chemistry may represent a method for preparing a silica network with a higher concentration of organic functionalites. Indeed, the Stöber process (sol-gel chemistry with an alcohol solvent and an ammonia catalyst) has proven effective for synthesizing N-diazeniumdiolate-modified silica particles of diverse size and NO storage capacity. See, for example, U.S. Publication No. 2009/0214618 (Schoenfisch et al.), which is herein incorporated by reference in its entirety. The advantage of the Stöber method over surface grafting is that the co-condensation provides uniform incorporation of the organic (i.e., NO donor) functionality throughout the resulting silica network as opposed to restricted functionalization at the surface alone. As a result, such particles may exhibit significantly increased NO storage.

SUMMARY OF THE INVENTION

A first aspect of the present invention comprises a method of forming S-nitrosothiol-functionalized co-condensed silica particles comprising:
  reacting a thiol-containing silane and a backbone alkoxysilane in a sol precursor solution that comprises water to form thiol-functionalized co-condensed silica particles, wherein the thiol-functionalized co-condensed silica particles comprise a polysiloxane matrix and at least some of thiol groups are present within the polysiloxane matrix; and
  reacting the thiol-functionalized co-condensed silica particles with a nitrosating agent to provide the S-nitrosothiol-functionalized co-condensed silica particles.

A second aspect of the present invention comprises S-nitrosothiol-functionalized monodisperse co-condensed silica particles having an average particle diameter in a range of about 10 nm to about 100 µm.

A further aspect of the present invention comprises S-nitrosothiol-functionalized co-condensed silica particles having an NO storage in a range of about 0.01 µmol to about 10 µmol NO per mg particle.

Another aspect of the present invention comprises a S-nitrosothiol-functionalized co-condensed silica particle comprising tertiary nitrosothiol functional groups.

A further aspect of the present invention comprises a compound having the following structure:

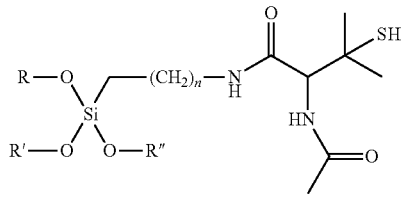

wherein R, R' and R" are each independently alkyl and n is 0 in a range of 0 to 10.

BRIEF DESCRIPTION OF THE DRAWINGS

The accompanying drawings, which are included to provide a further understanding of the invention and are incorporated in and constitute a part of this application, illustrate certain embodiment(s) of the invention.

DETAILED DESCRIPTION OF EMBODIMENTS OF THE INVENTION

Figure 1:
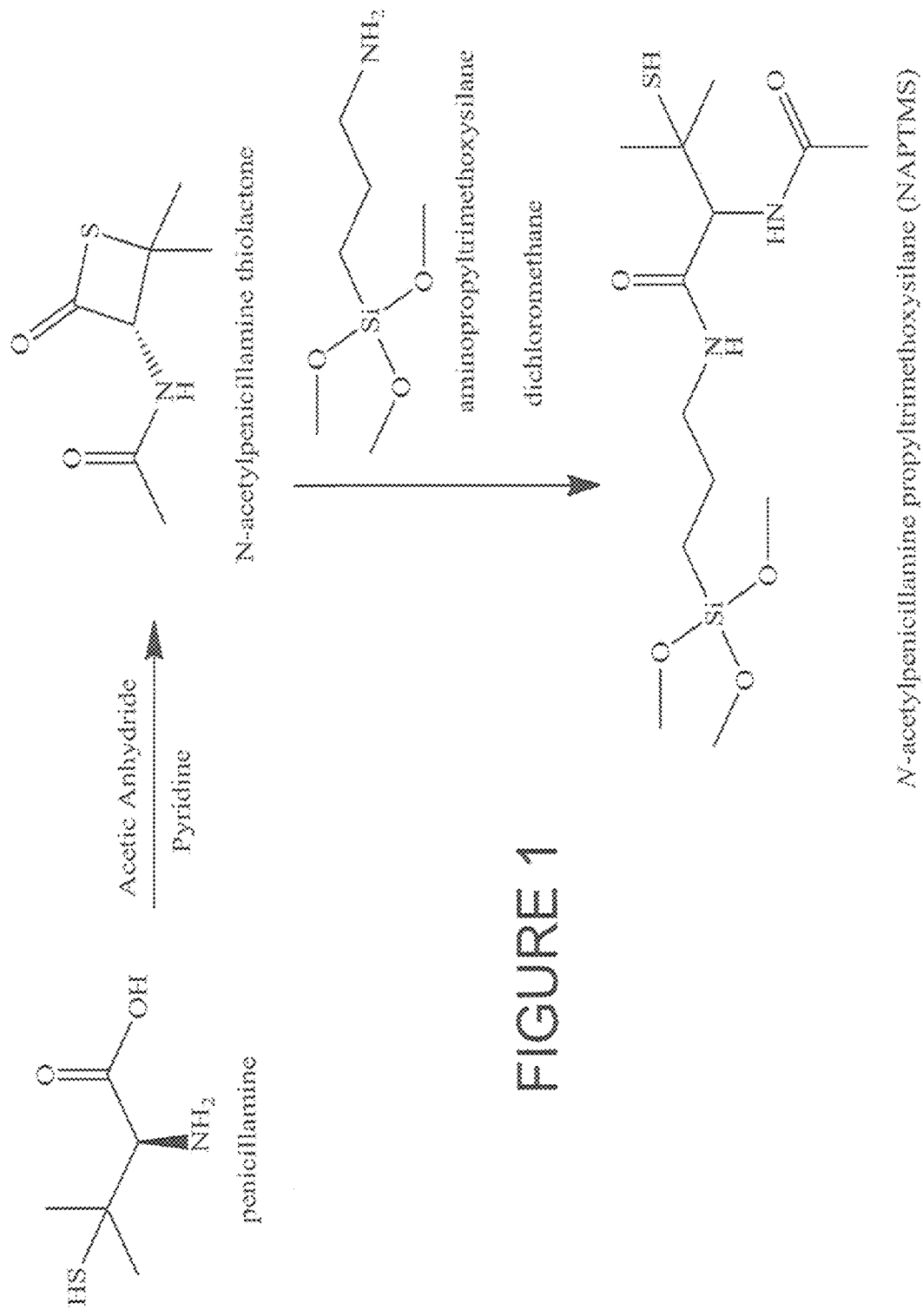
FIG. 1 provides a scheme for the synthesis of N-acetylpenicillamine propyltrimethoxysilane (NAPTMS).

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl)hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

The term "mercapto" or "thio" refers to the —SH group.

Provided herein according to some embodiments of the invention are methods of forming co-condensed silica particles via the Stöber process. See, e.g., Stöber, W.; Fink, A.; Bohn, E. *J. Colloid Intel face Sci.* 1968, 26, 62 (incorporated by reference herein in its entirety). Particle formation under the Stöber process proceeds upon hydrolysis and condensation of silane precursors where the relative hydrolysis rates for the precursors dictate both the speed of particle growth and the likelihood of each silane's incorporation into the silica network. Excessive disparities between reaction rates of different silanes may lead to absence of particle formation upon attempted co-condensation.

Provided according to some embodiments of the invention are methods of forming S-nitrosothiol-functionalized co-condensed silica particles that include reacting a thiol-containing silane and a backbone alkoxysilane in a sol precursor solution that includes water to form thiol-functionalized co-condensed silica particles, wherein the thiol-functionalized co-condensed silica particles include a polysiloxane matrix and at least some of thiol groups are present within the polysiloxane matrix. In some embodiments of the invention, the methods further include reacting the thiol-functionalized co-condensed silica particles with a nitrosating agent to provide the S-nitrosothiol-functionalized co-condensed silica particles.

Any suitable thiol-containing silane may be used. In some embodiments, the thiol-containing silane includes a primary thiol, in some embodiments, a secondary thiol, and in some embodiments, a tertiary thiol. Combinations of different silanes may also be used. A suitable thiol-containing silane will be a silane that will allow for particle formation, and in some embodiments, monodisperse particle formation. Thus, some thiol-containing silanes may be suitable with some backbone alkoxysilanes and not suitable with others. In some embodiments, the primary thiol-containing silane is mercaptopropyltrimethoxysilane. In some embodiments, the tertiary thiol alkoxysilane has the following structure: (OR)(OR')(OR")Si($R^x$), wherein R, R' and R" are each independently H, alkyl or substituted alkyl and $R^x$ is functional group that comprises a tertiary thiol group. In particular embodiments, the tertiary thiol alkoxysilane has the structure:

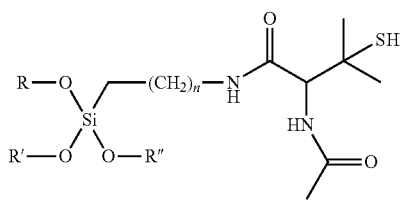

wherein R, R' and R" are each independently H, alkyl or substituted alkyl and n is 0-10. In some embodiments, R, R' and R" are each independently alkyl and n is 0-5. Furthermore, in particular embodiments of the invention, the tertiary thiol is a compound having the structure:

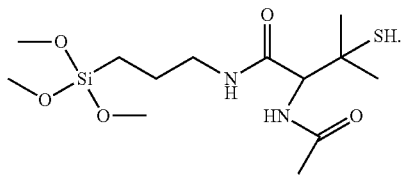 [SMILES: CO[Si](CCCNC(=O)C(NC(C)=O)C(C)(C)S)(OC)OC]

Any suitable backbone alkoxysilane may be used. As used herein, the term "backbone alkoxysilane" refers to an alkoxysilane that does not contain a thiol functional group. Examples include tetramethoxysilane, tetraethoxysilane, methyltrimethoxysilane, methyltriethoxysilane and butyltrimethoxysilane. A suitable backbone silane will be a silane that will allow for particle formation, and in some embodiments, monodisperse particle formation.

Any suitable concentration of water may be used. In some embodiments, the water concentration in the sol precursor solution is in a range of about 8 M to about 32.5 M.

In some embodiments, a catalyst, such as an ammonia catalyst, is included in the sol precursor solution. Any suitable concentration of catalyst may be used. However, in some embodiments, an ammonia catalyst is included in the sol precursor solution, in some embodiments, at a concentration in a range of about 1.9 M to about 5.5 M.

In particular embodiments of the invention, mercaptopropyltrimethoxysilane and tetramethoxysilane are reacted in the presence of water and an ammonia catalyst to form thiol-functionalized co-condensed silica particles. In some embodiments, the reaction occurs in a solution that includes mercaptopropyltrimethoxysilane and tetramethoxysilane at a total silane monomer concentration in a range of about 0.1 M to about 0.4 M, wherein the silane monomer includes about 25 to about 85 mol % mercaptopropyltrimethoxysilane. In some embodiments, water is present in the solution at a concentration in a range of about 8.0 to about 32.5 M and the ammonia catalyst is present at a concentration in a range of about 1.9 M to about 5.5 M.

In some embodiments of the invention, mercaptopropyltrimethoxysilane and tetraethoxysilane are reacted in the presence of water and an ammonia catalyst to form thiol-functionalized co-condensed silica particles. In some embodiments, the reaction occurs in a solution that includes mercaptopropyltrimethoxysilane and tetraethoxysilane at a total silane monomer concentration in a range of about 0.1 M to about 0.4 M, wherein the silane monomer includes about 75 to about 85 mol % mercaptopropyltrimethoxysilane. In some embodiments, water is present in the solution at a concentration in a range of about 8.0 to about 32.5 M and the ammonia catalyst is present at a concentration in a range of about 1.9 M to about 5.5M.

In some embodiments, methods of forming thiol-functionalized co-condensed silica particles include reacting a tertiary thiol-containing silane and a backbone alkoxysilane in the presences of water and an ammonia catalyst to form thiol-functionalized co-condensed silica particles. In some embodiments, the reaction occurs in a solution that includes tertiary thiol-containing silane and alkoxysilane at a total silane monomer concentration in a range of about 0.1 M to about 0.4 M, wherein the silane monomer includes about 25 to about 85 mol % tertiary thiol-containing silane. In some embodiments, water is present in the solution at a concentration in a range of about 8.0 to about 32.5 M and the ammonia catalyst is present at a concentration in a range of about 1.9 to about 5.5 M.

The sol precursor solution may also be stirred/agitated as known to those of skill in the art, and other additives or silane monomers used in sol chemistry may be included in some embodiments of the invention.

In some embodiments of the invention, methods provided herein may be used to form nitrosothiol-functionalized co-condensed silica particles, which in some embodiments, are monodisperse. As used herein, the term "monodisperse" refers to particles having a uniform particle size, in some embodiments, having an average particle diameter ±100 nm as measured from electron micrographs; a Z-average ±60 nm as measured from dynamic light scattering; and/or having a polydispersity index ≤0.1 as measured via dynamic light scattering. In some embodiments, the methods described herein provide monodisperse particles having an average particle diameter of less than 100 microns, and in some embodiments, less than 1 micron. In particular embodiments, the methods used herein may provide monodisperse particles having an average particle diameter in a range of about 10 nm to about 100 μm. In some embodiments, the particles have an average particle diameter in a range of about 200 to about 700 nm.

Any suitable method of nitrosating the thiol-functionalized co-condensed silica particles may be used. Further, any suitable nitrosating agent may be used. However, in some embodiments, the nitrosating agent includes acidified sodium nitrite, alkyl nitrites, including tertbutyl nitrite and isopentyl nitrite, and various nitrogen oxides including nitrous oxide, $N_2O_3$, $N_2O_4$ and $NO_2$. Examples of nitrosation may be found in Williams, D. L. H. *Acc. Chem. Res.* 1999, 32, 869, the contents of which are incorporated herein by reference in their entirety.

In some embodiments of the invention, the nitrosation chemistry conserves particle size integrity and yields monodisperse S-nitrosothiol-functionalized co-condensed silica particles. No changes in particle size have been observed following addition of the nitric oxide functionality to the macromolecular structure, a drawback that has been observed with other nitrosothiol-modified macromolecular donors. Furthermore, as shown below in the Examples, the thiol-functionalized co-condensed silica particles may be sonicated prior to nitrosation without deleteriously affecting the NO storage and/or morphology of the particles.

The co-condensed silica particles may include S-nitrosothiol groups throughout the particle, and as such, may provide enhanced NO storage properties. For example, in some embodiments of the invention, provided are S-nitrosothiol-functionalized co-condensed silicas particles that have an NO storage in a range of about 0.01 μmol to about 10 μmol NO per mg particle, and in some embodiments, 0.09 μmol to about 4.40 μmol NO per mg particle.

The incorporation of the S-nitrosothiol groups throughout the interior of the silica particle structure may also afford unexpected stability. Glutathione and other thiols are known to one skilled in the art to be a vial trigger for RSNO decomposition and release a variety of NOx species. In some embodiments of the invention, the low porosity of the S-nitrosothiol-functionalized co-condensed silica particles protect the RSNO donors from premature decomposition by glutathione or other blood components, adding a level of nitric oxide stability when used in drug delivery applications.

EXAMPLES

Preparation of NAPTMS

Synthesis of N-Acetyl Penicillamine (NAP) Thiolactone

Acetic anhydride (96 mmol, 9.80 g) was added dropwise to a well stirred solution of D-(−) penicillamine (40 mmol, 5.97 g) in pyridine (50 mL) at 0° C. After 30 min, the flask was removed from ice and allowed to stir at room temperature for 15 h. The resultant orange solution was partitioned between chloroform and dilute HCl and washed 4× with dilute HCl. After drying over MgSO$_4$, the organic phase was evaporated to yield an orange residue. The residue was first dissolved in absolute ethanol (20 mL), and then precipitated in pentane at −78° C. The light yellow crystalline product was isolated by filtration (2.07 g, 30%). $^1$H NMR (CDCl$_3$) δ1.65 (s, CH$_3$), 1.86 (s, CH$_3$), 2.05 (s, NHCOCH$_3$), 5.68-5.70 (d, CH(CH$_3$)$_2$), 6.56 (NHCOCH$_3$). $^{13}$C NMR (CDCl$_3$) δ 22.52 (NHCOCH$_3$), 26.20 (CH(CH$_3$)$_2$), 30.22 (CH(CH$_3$)$_2$), 51.23 (CH), 169.37 (NHCOCH$_3$), 192.21 (SCO).

Synthesis of N-Acetyl Penicillamine Propyltrimethoxysilane (NAPTMS). APTMS (10 mmol, 1.78 g). was added to a stirring solution of NAP thiolactone (10 mmol, 1.72 g) in methylene chloride (20 mL). The light yellow solution was stirred for 4 h at room temperature before distillation of the methylene chloride to yield NAPTMS as a viscous clear oil. $^1$H NMR (CDCl$_3$) δ 0.54 (t, SiCH$_2$), 1.24 and 1.39 (s, CH(CH$_3$)$_2$SH), 1.54 (m, SiCH$_2$CH$_2$), 1.96 (s, NHCOCH$_3$), 2.96 and 3.21 (m, SiCH$_2$CH$_2$CH$_2$), 3.44 (s, Si(OCH$_3$)$_3$), 4.63 (d, CHC(CH$_3$)$_2$SH), 6.99 (d, CHNHCOCH$_3$), 7.70 (t, CH$_2$NHCOCH). $^{13}$C NMR (CDCl$_3$) δ □6.59 (SiCH$_2$), 22.42 and 22.97 (CH(CH$_3$)$_2$SH), 28.64 (NHCOCH$_3$), 30.80 (SiCH$_2$CH$_2$), 41.93 (CHC(CH$_3$)$_2$SH), 46.23 (SiCH$_2$CH$_2$CH$_2$), 50.35 (Si(OCH$_3$)$_3$), 60.32 (CHC(CH$_3$)$_2$SH), 169.64 (CHNHCOCH$_3$), 170.17 (CHCONH).

Figure 2:
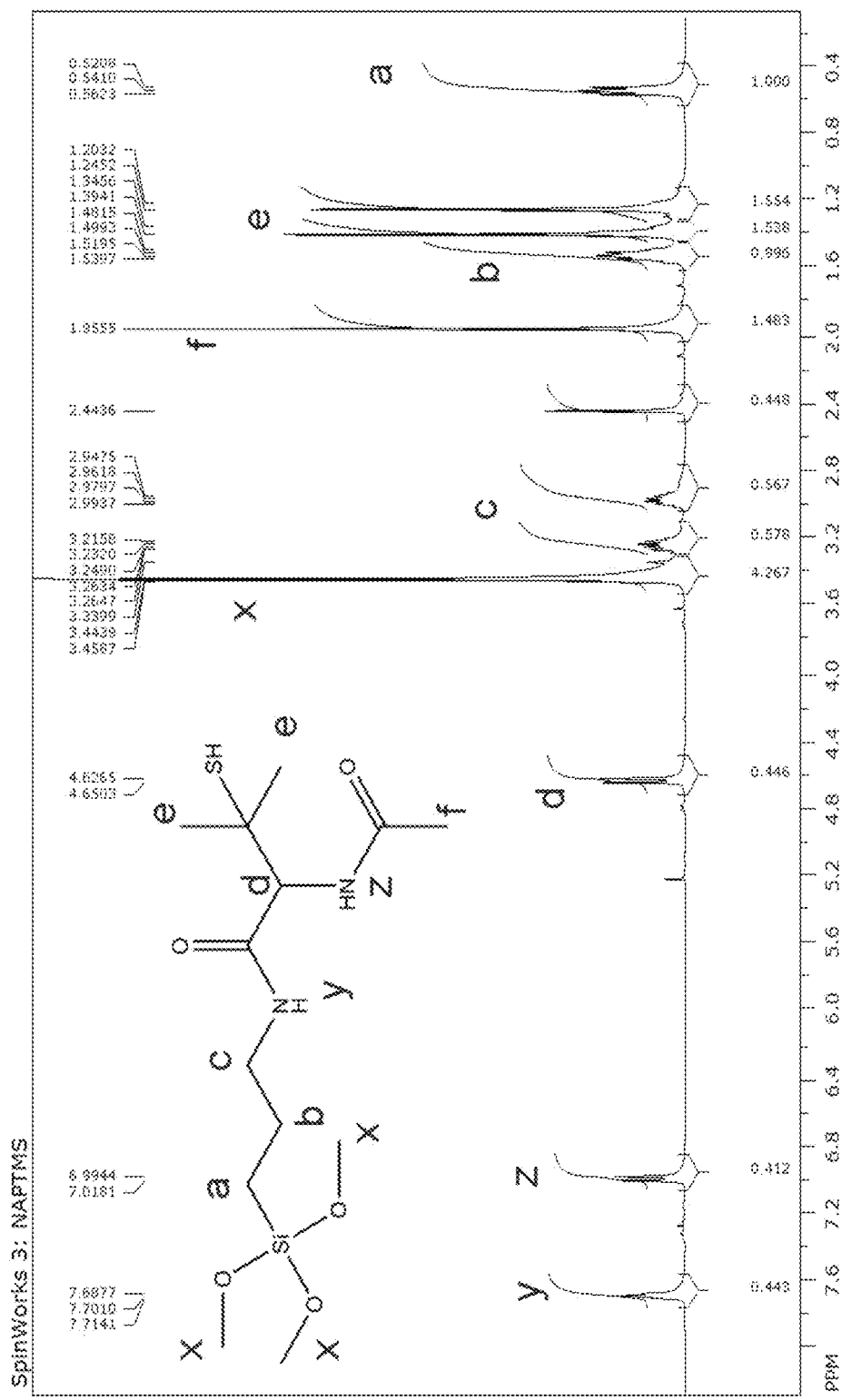
FIG. 2 provides an $^1$H NMR spectrum of the NAPTMS compound.

The preparation of tertiary thiol-based precursors was investigated for the development of biomedical devices/therapeutics with continuous and photoactivatable NO release. A NAP thiolactone was thus synthesized to design such a precursor for the synthesis of NO-releasing xerogels. Penicillamine was reacted in the presence of acetic anhydride to generate the NAP thiolactone in situ. After characterization by $^1$H and $^{13}$CNMR, the NAP thiolactone was directly coupled with APTMS to result in a tertiary thiol-bearing silane, referred to as NAPTMS (see FIG. 1). Successful synthesis of this tertiary thiol-bearing silane was verified via $^1$HNMR characterization (FIG. 2).

Example 1

MPTMS

Ratios of mercaptosilane and alkoxysilane (25-85 mol % MPTMS, balance TMOS or TEOS) were added either as a bolus injection or dropwise via a Kent Scientific Genie Plus syringe pump at a flow rate of 0.25-3.0 mL/min through an 18.5 gauge needle to a solution of ethanol, water, and ammonium hydroxide. Solution was stirred for 2 h at room temperature, collected via centrifugation at 4500 rpm (10 mins), washed twice with 40 mL EtOH, recollected, and dried overnight at ambient conditions.

Our initial attempt to synthesize thiol-containing silica particles was based on a bolus injection of 3-mercaptopropyltrimethoxysilane (MPTMS) and alkoxysilane into EtOH/NH$_4$OH solution, The resulting concentrations of ammonia, water and total silane were 3.3, 8.0, and 0.2 M, respectively. Tetramethoxysilane (TMOS) proved to be a sufficient backbone silane for co-condensation with MPTMS as their combination (at various mole percentages) resulted in the formation of a white precipitate. (~300 mg yield).

As indicated by solution turbidity, a marked increase in reaction time was observed upon increasing the concentration of MPTMS up to 85 mol %. At this concentration, the time to form a visible product after combining the silanes was roughly 15 min. Product formation at MPTMS concentrations >85 mol % was not observed. The inability to form particles at greater MPTMS concentrations may be attributed to the disparate hydrolysis rates between the silanes, suggesting that co-condensation requires a minimum concentration of the more readily hydrolyzable silane (i.e., TMOS) to initiate particle growth.

Materials synthesized via the co-condensation of MPTMS and tetraethoxysilane (TEOS) formed only in the concentration range of 75-85 mol % MPTMS. In contrast to the TMOS system, products with lower concentrations of MPTMS (e.g., 25 mol %) did not form using TEOS as a backbone, even at prolonged reaction times (up to 48 h).

Example 2

MPMDMS

Another thiol-functionalized monomer, 3-mercaptopropylmethyldimethoxysilane (MPMDMS), was also investigated. Unfortunately, the product yield (~5 mg) formed using MPMDMS with either TMOS or TEOS was significantly lower than MPTMS. The substitution of one of the hydrolyzable methoxy groups with a nonhydrolyzable methyl linkage in MPMDMS (vs. MPTMS) appears to decrease the resulting hydrolysis rate under basic conditions, possibly due to the inductive effect of electron density donation to the Si atom. As a result, the reaction with hydroxide anion to hydrolyze the silane may be inhibited. Particle formation may even be further limited as each MPMDMS molecule is capable of forming only two siloxane bridges. Consequently, particle formation using MPMDMS was unsuccessful.

Example 3

Characterization of First Generation Mercaptosilane-Based Silica Particles

Solid-state cross polarization/magic angle spinning (CP/MAS) 29Si (71.548 MHz frequency) nuclear magnetic resonance (NMR) spectroscopy was performed on a Bruker 360 MHz DMX spectrometer (Billerica, Mass.). Particles were packed into 4 mm rotors and spun at 8.0 kHz. Spectra were collected at 5000 scans with the determination of chemical shifts in parts per million relative to an external TMS standard. Nitric oxide release was measured in real time (1 sec intervals) using 5 a Sievers NOATM 280i Chemiluminescence Nitric Oxide Analyzer (NOA) (Boulder, Colo.). Calibration of the NOA was performed with both air passed through a Sievers NO zero filter and 26.39 ppm NO gas (balance $N_2$). Nitric oxide-releasing particles were immersed in 25 mL of deoxygenated solution and sparged with an 80 mL min−1 $N_2$ stream. Additional $N_2$ was supplied to the reaction flask to match the collection rate of the NOA at 200 mL min−1.

Temperature control was maintained using a water bath at 37° C. Thermal and photo-initiated NO release were studied by conducting the experiments in 500 µM DTPA (pH 7.4 PBS) to chelate trace copper and illuminating the sample flask with 60, 100, and 200 W incandescent bulbs, respectively. Copper-initiated NO release was studied by adding the particles to 25 mL of 10 or 25 µM $CuBr_2$(aq). The NOA sample flask was shielded from light with aluminum foil for experiments where light was not the intended initiator of NO release. Particle size was determined using a Zetasizer Nano ZS Particle Size and Zeta Potential Dynamic Light Scattering (DLS) Instrument (Malvern, UK). Samples were suspended in PBS at a concentration of 1 mg mL$^{-1}$ and sonicated for 15 min prior to analysis. Scanning electron micrographs were recorded on a Hitachi S-4700 Scanning Electron Microscope (Pleasanton, Calif.).

Figure 3:
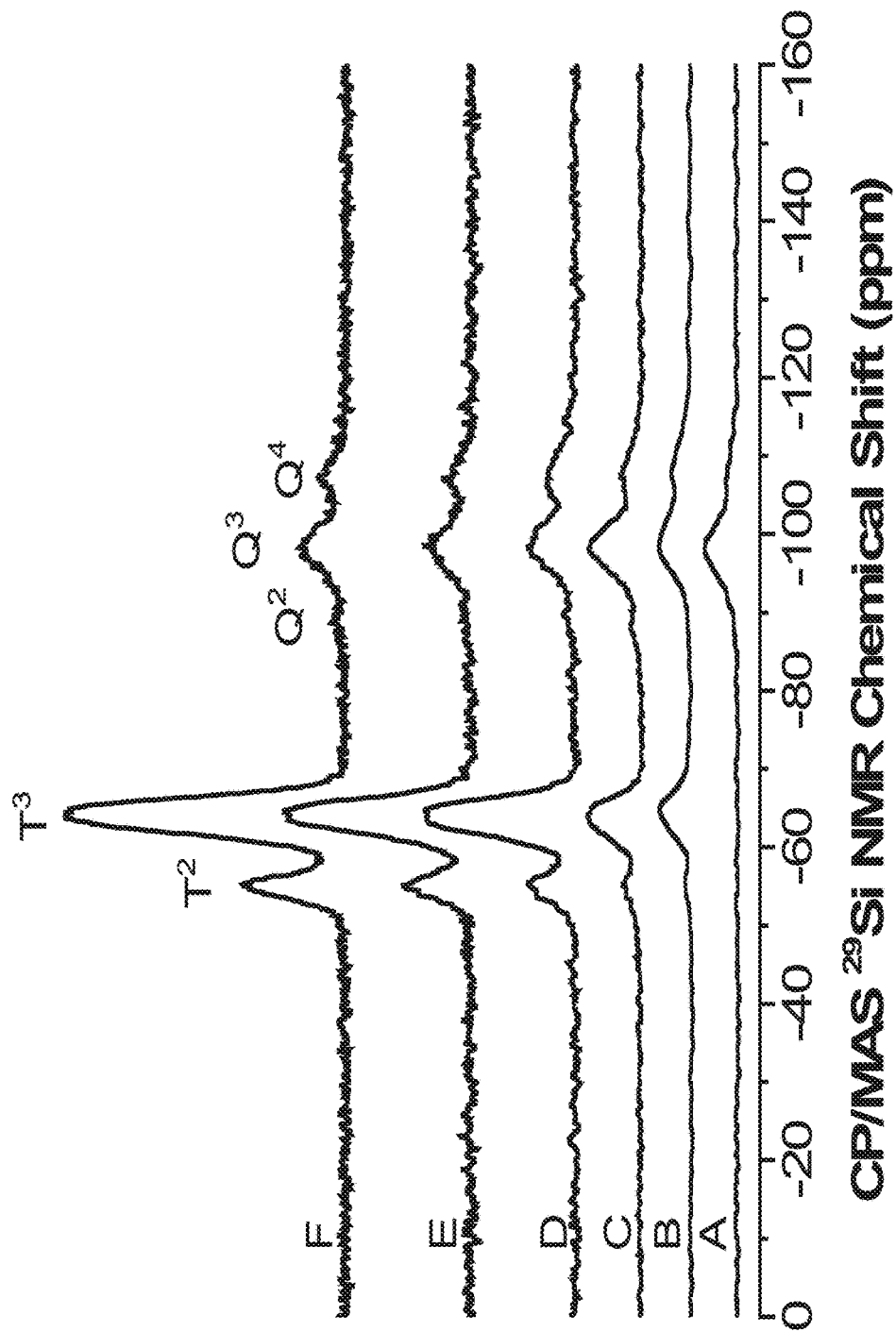
FIG. 3 shows a solid-state cross polarization/magic angle spinning (CP/MAS) $^{29}$Si NMR spectra of silica synthesized with (A) 0, (B) 25, (C) 40, (D) 60, (E) 75, and (F) 85 mol % MPTMS (balance TMOS). The Q and T bands have been designated.

To confirm the incorporation of mercaptosilane within the silica network and compare various compositions, solid-state $^{29}Si$ cross polarization/magic angle spinning nuclear magnetic resonance (CP/MAS NMR) was used to characterize the MPTMS/TMOS products as a function of MPTMS concentration: Silicon atoms of tetraalkoxysilanes appear in the NMR spectra as $Q^n$ bands while those of organotrialkoxysilanes appear as $T^n$ bands. In both cases, n denotes the number of siloxane bonds attached to the Si atom. The greater number of siloxane bonds to the Si atom, the further the NMR band shifts upfield. FIG. 3 shows silica synthesized with (A) 0, (B) 25, (C) 40, (D) 60, (E) 75, and (F) 85 mol % MPTMS (balance TMOS). Particles synthesized entirely from TMOS exhibited only Q bands. With increasing MPTMS concentration in the solution used to prepare the particles, the T bands increased relative to the Q bands, confirming greater incorporation of MPTMS in the silica particle.

Sulfur weight percent of each composition was determined using elemental analysis and further corroborated the covalent incorporation of the mercaptosilane. The weight percent of sulfur in the silica was 4.92, 7.11, 11.67, 13.56 and 17.30 for the 25, 40, 60, 75 and 85 mol % MPTMS (balance TMOS) compositions, respectively. The TEOS-based particles were found to have sulfur weight percents of 16.15 and 19.34 for 75 and 85 mol % MPTMS, respectively. As expected, the weight percent of sulfur increased linearly with increasing MPTMS concentration in the initial solution.

Dynamic light scattering (DLS) measurements indicated that the sample was too polydisperse to accurately measure the particle size. Scanning electron micrographs (SEMs) further indicated that the thiol-containing silica was polydisperse and exhibited nonspherical morphology more indicative of colloidal silica than individual particles. (data not shown).

Example 4

Variation of Water, Ammonia and Silane Concentrations and Feed Rate

We systematically varied synthetic parameters (i.e., water, ammonia, and silane concentrations) to tune the resulting particle morphology and achieve a more spherical shape. The composition of 25 mol % MPTMS (balance TMOS) was chosen as the model system for comparison due to minimal organic character.

For MPTMS particles, we found that increasing the water content from 8.0 to 16.2 M promoted the formation of spherical particles and prevented aggregation/fusion. Lower ammonia concentrations were shown to result in particles that lacked spherical shape and aggregated. Thus, we discovered that the ratio of water and ammonia to silane was a critical factor during particle synthesis. Upon considering all the data, we determined that the most spherical and monodisperse particles were the 25 mol % MPTMS (balance TMOS) particles were formed using 5.5 M ammonia, 0.1 M total silane, and 16.2 M water. Of note, the product yield (~70 mg) with this synthesis was lower than that obtained for the polydisperse colloidal silica. The decreased yield was due to the 4-fold decrease in the silane concentration used in the optimized synthesis.

Figure 4:
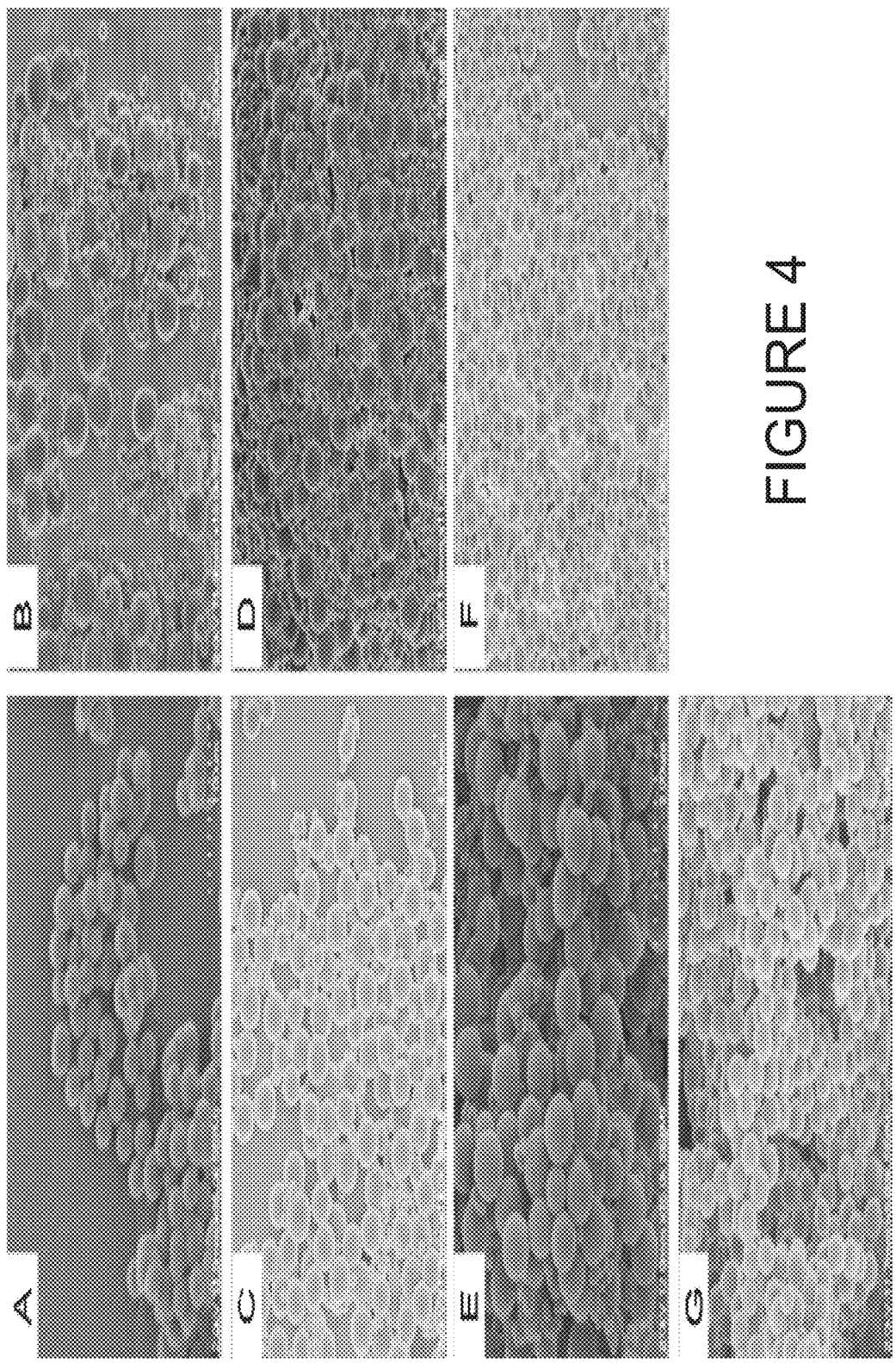
FIG. 4 shows the scanning electron micrographs of (A) 25, (B) 40, (C) 60, (D) 75 and (E) 85 mol % MPTMS (balance TMOS) and (F) 75 and (G) 85 mol % MPTMS (balance TEOS) particles synthesized with 16.0 M water, 5.5 M ammonia, and 0.1 M silane.

Next, the concentration of MPTMS in the solution was increased to enhance the degree of thiol functionality and potential NO storage of the particles. FIG. 4 depicts the resulting particles as the concentration of MPTMS was increased from 25-85 mol % and backbone alkoxysilane varied between TMOS and TEOS. The particles were synthesized with 16.0 M water, 5.5 M ammonia, and 0.1 M silane.

As with the polydisperse colloidal silica system, the formation of particles was not observed for 25-60 mol % MPTMS (balance TEOS). Only 75 and 85 mol % MPTMS concentrations yielded particles with TEOS, illustrating how disparities in hydrolysis and condensation kinetics adversely affect and hinder particle formation. The 75 mol % MPTMS (balance TEOS) particles formed in a narrow size distribution and exhibited spherical morphologies (FIG. 4F). In contrast, 85 mol % MPTMS (balance TEOS) particles appeared aggregated (FIG. 4G). When using TMOS, 25 mol % MPTMS was the only concentration that yielded spherical, monodisperse particles (FIG. 4A). Particles with ≥40 mol % MPTMS (balance TMOS) exhibited ideal morphologies, but with concomitant bimodal size distributions (FIG. 4B-E).

Figure 5:
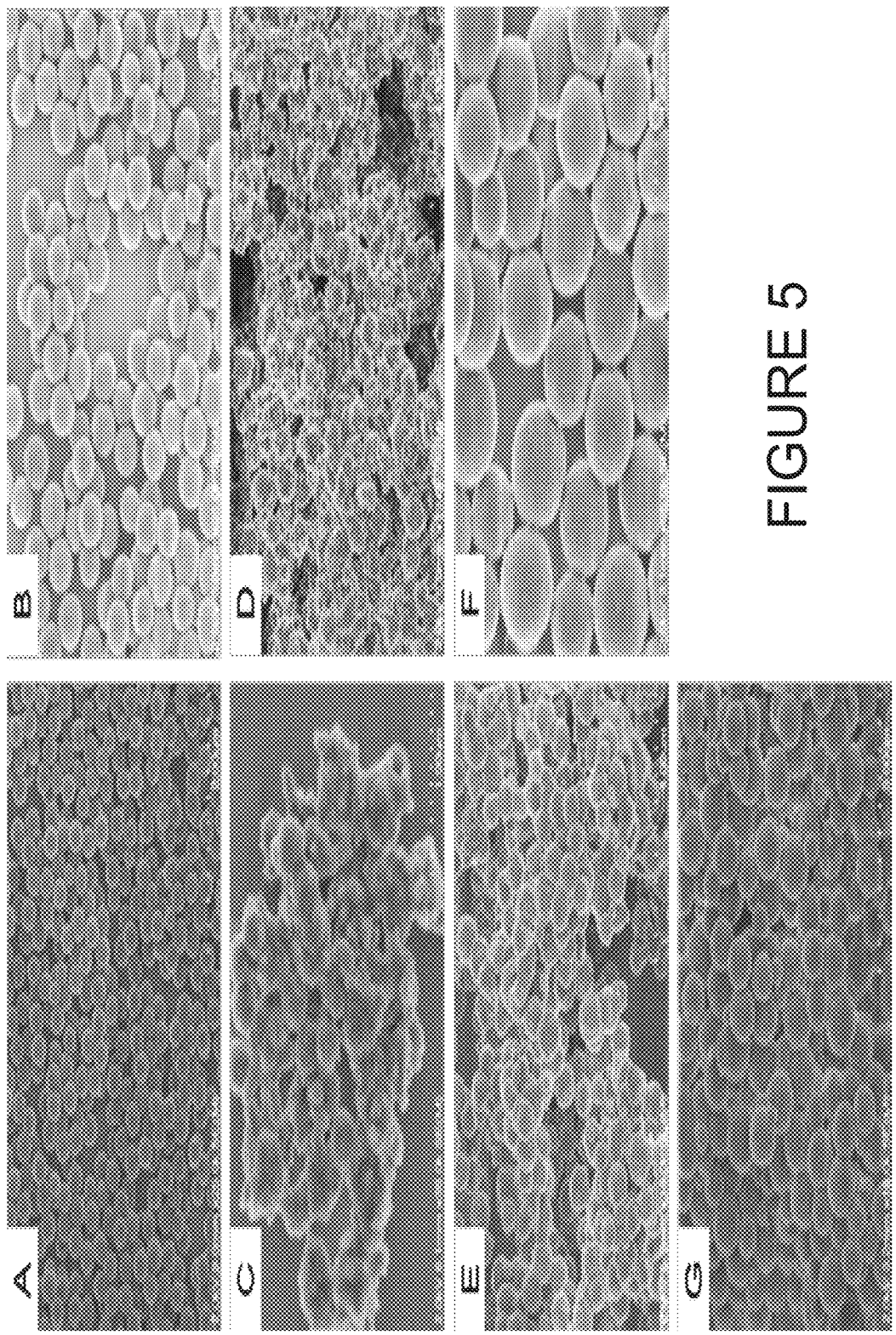
FIG. 5 shows the scanning electron micrographs of (A) 25, (B) 40, (C) 60, (D) 75 and (E) 85 mol % MPTMS (balance TMOS) and (F) 75 and (G) 85 mol % MPTMS (balance TEOS) particles synthesized via a semi-batch process with a silane feed rate of 0.5 nit $\text{min}^{-1}$.

To remedy the bimodal size distribution that was observed for certain MPTMS compositions, we evaluated the effect of a silane feed rate of 0.5 mL min$^{-1}$ on particle morphologies throughout the range of compositions (FIG. 5). The slower feed rate improved the dispersity of the already narrow size distribution for 25 mol % MPTMS (FIG. 5A). A pronounced improvement in the monodispersity was also noted for 40 mol % MPTMS (balance TMOS, FIG. 5B), with SEM indicating a particle diameter of 293±24 nm. Slower silane feed rates (e.g., 0.25 mL min$^{-1}$) resulted in slight monodispersity improvements (data not shown), but at lower yields (e.g., ~40 vs. 70 mg for 40 mol % MPTMS (balance TMOS) composition). Thus, 0.5 mL min$^{-1}$ was determined to be the optimal feed rate as it allowed for a balance between sufficient particle yield and monodispersity. Similar to 25 mol % MPTMS (balance TMOS), the monodispersity of 75 mol % MPTMS (balance TEOS) improved, while the 85 mol % MPTMS (balance TEOS) system remained aggregated (FIGS. 5F and 5G, respectively).

Additionally, the product yield increased to ~170 mg for these two compositions and can be attributed to the greater concentration of the larger MPTMS in the particles. Unfortunately, the semi-batch process proved problematic for 60, 75, and 85 mol % MPTMS (balance TMOS) particles. As shown in FIG. 5C-E, the slowed silane addition resulted in both aggregation and the formation of a large silica network rather than monodisperse, spherical particles. To examine this phenomenon further, silane feed rates were varied (0.25-3.0 mL min$^{-1}$) for 60 mol % MPTMS (balance TMOS). Feed rates <2.0 mL min$^{-1}$ resulted in polydisperse, aggregated silica, while faster feed rates (2.0-3.0 mL min$^{-1}$) produced particles of a bimodal size (data not shown).

Figure 6:
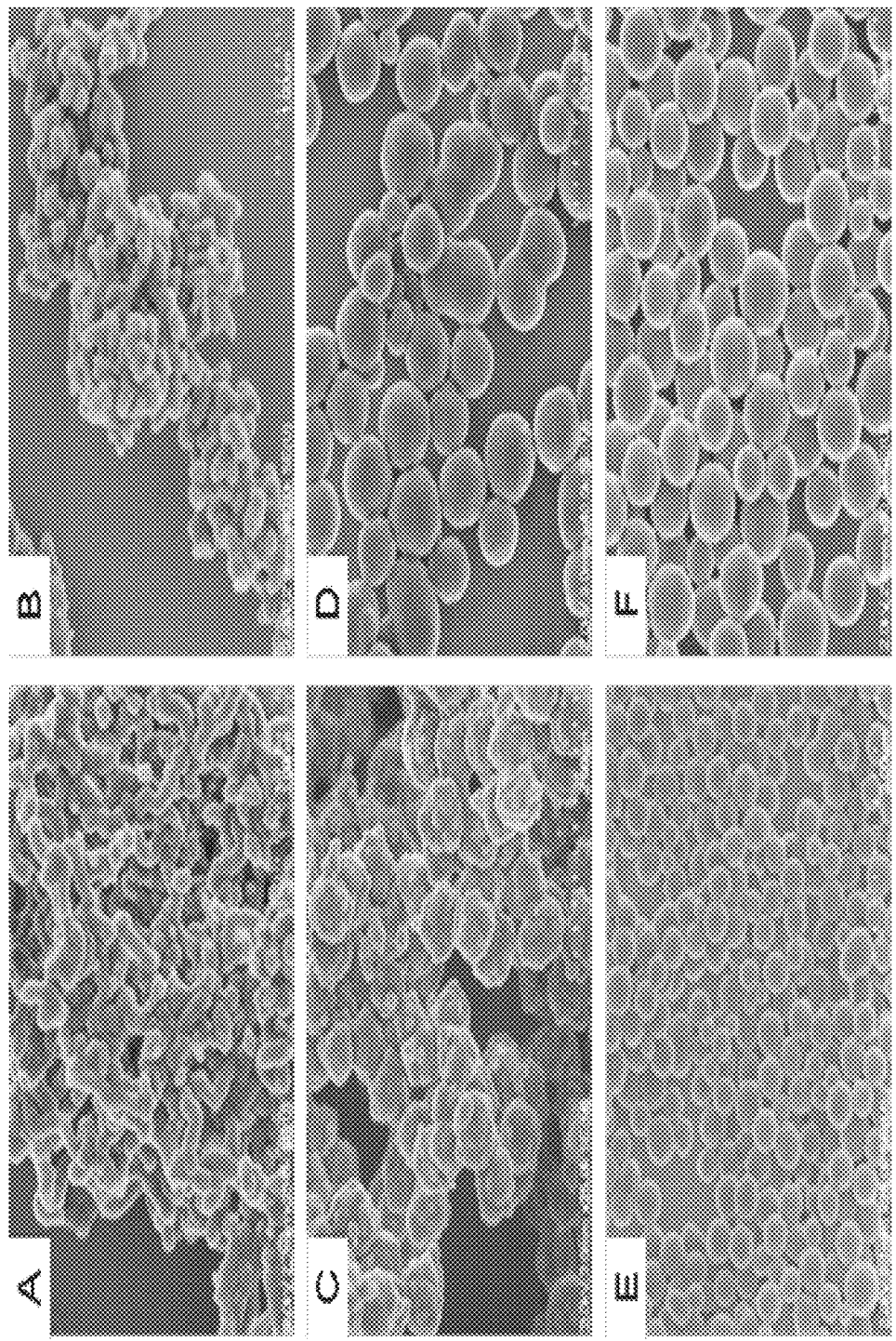
FIG. 6 shows the scanning electron micrographs of 75 mol % MPTMS (balance TEOS) synthesized with (A) 47.0, (B) 42.0, (C) 40.6, (D) 36.5, (E) 32.5, and (F) 24.9 M water.

We then attempted to decrease the size of the particles to improve particle monodispersity. The 75 mol % MPTMS (balance TEOS) particles were chosen as a model system to examine the effect of the water concentration on particle size and morphology. As shown in FIG. 6, 75 mol % MPTMS (balance TEOS) was synthesized with (A) 47.0, (B) 42.0, (C) 40.6, (D) 36.5, (E) 32.5, and (F) 24.9 M water. Water concentrations ≥40.6 M favored rapid silane hydrolysis and condensation kinetics, leading to a highly condensed network rather than discrete, spherical particles. At a water concentration of 36.5 M, discrete particles were formed, but with morphologies featuring excessive aggregation. Monodisperse particles (333±48 nm) were first observed at a slightly lower water concentration (32.5 M). Particle size increased with decreasing water concentrations (456±68 nm and 635±63 nm for 24.9 and 16.2 M, respectively). Furthermore, the smaller particle sizes were accompanied with slightly lower yields for each composition. The yields for 75 mol % MPTMS (balance TEOS) particles were ~65, 150, and 170 mg for water concentrations of 32.5, 24.9, and 16.2 M, respectively. The differences in yield may be factors of the efficiency of particle collection (i.e., centrifugation rpm and duration) for the smaller particles rather than chemical differences.

Figure 7:
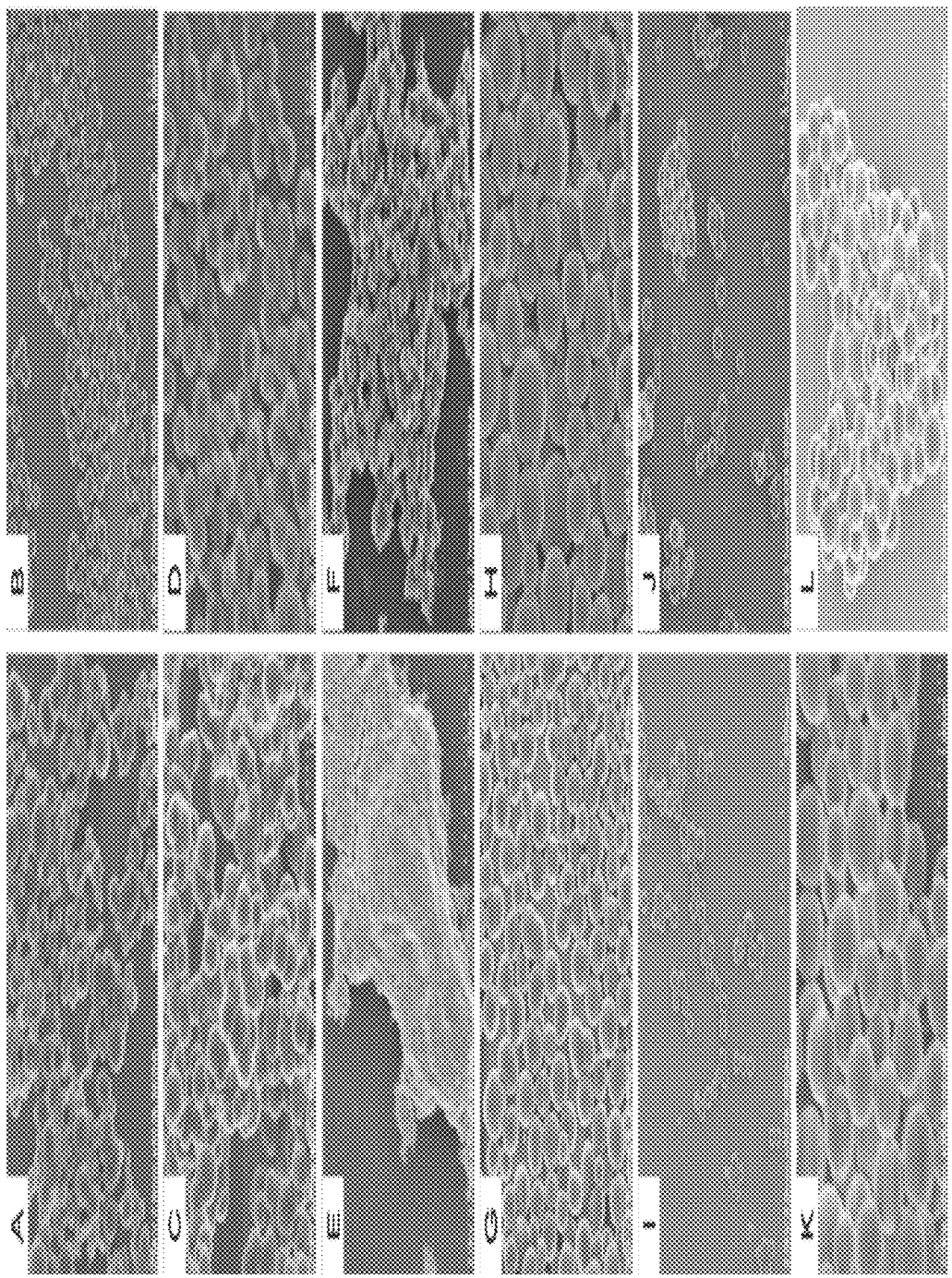
FIG. 7 shows the scanning electron micrographs of (A-B) 25, (C-D) 40, (E-F) 60, (G-H) 75, and (1-J) 85 mol % MPTMS (balance TMOS) and (K-L) 85 mol % MPTMS (balance TEOS) particles synthesized with (A, C, E, F, G, I, K) 32.5 and (B, D, F, H, J, L) 24.9 M water.

The appropriate water concentrations (32.5 and 24.9 M) were next used to tune particle size and reduce the bimodal distribution characteristic of the 60, 75, and 85 mol % MPTMS (balance TMOS) particles. As shown in FIG. 7, the intermediate water concentration (24.9 M) yielded particles with sizes of 179±22 and 196±25 nm for the 25 and 40 mol % MPTMS (balance TMOS) compositions, respectively. The greater water concentration (32.5 M) drastically increased the reaction kinetics for the mostly TMOS-based systems, resulting in highly-fused silica networks. Increasing the concentration of MPTMS (75 mol %) yielded monodisperse, spherical particles of 363±51 and 279±49 nm using 24.9 and 32.5 M water, respectively. Aggregated and fused particles were formed for the greatest MPTMS concentration (85 mol %) when using 24.9 M water. However, monodisperse particles (440±84 nm) were formed when synthesized with 32.5 M water.

The TEOS-based counterpart to this system behaved similarly by yielding only discrete particles (506±77 nm) when synthesized with the higher water concentration. At lower water amounts, the formation of aggregated particles was noted. The trend of decreasing particle yield with increasing water content that was observed for the 75 mol % MPTMS (balance TEOS) composition was mirrored for all other compositions evaluated. The yields for the 75 mol % (balance TMOS) particles decreased from ~120 to 60 mg upon increasing the water content from 24.9 to 32.5 M. Likewise, the 25 mol % MPTMS (balance TMOS) particle yield decreased from ~90 to 20 mg while the 40 mol % MPTMS system exhibited a decrease from ~50 to 9 mg upon increasing the water concentration from 16.2 to 24.9 M. The yields for both 85 mol % MPTMS compositions (i.e, TMOS and TEOS balance) at a water concentration of 32.5 M were ~160 mg. Perhaps of greatest significance, the elevated water concentrations used to synthesize the thiol-modified particles successfully resolved the bimodal nature of certain compositions not resolvable using a semi-batch process alone. Of note, 60 mol % MPTMS (balance TMOS) was the only composition that consistently yielded particles of a bimodal nature. Increasing the water content regardless of addition method (bolus vs. semi-batch) resulted in a highly-fused silica network.

Particle sizes were also measured by DLS to corroborate particle monodispersity and size measured using SEM. As shown in Table 1, the DLS measurements were in agreement with the sizes calculated from the SEM images. The slightly increased average diameters observed with DLS may be attributed to particle hydration (DLS measurements conducted in solution). Like SEM, the DLS measurements indicated a narrow size distribution, as evidenced by low polydispersity indices for each composition.

TABLE 1

| Particle composition (mol % MPTMS) | Water content (M) | Particle size[a] (nm) | Z-Average size[b] (nm) | Polydispersity index |
|---|---|---|---|---|
| 75% (balance TEOS) | 32.5 | 333 ± 48 | 416.2 ± 23.4 | 0.027 |
| 75% (balance TEOS) | 24.9 | 456 ± 68 | 529.6 ± 23.7 | 0.018 |
| 75% (balance TEOS) | 16.2 | 635 ± 63 | 718.0 ± 51.7 | 0.046 |
| 85% (balance TEOS) | 32.5 | 506 ± 77 | 668.7 ± 46.0 | 0.040 |
| 25% (balance TMOS) | 24.9 | 179 ± 22 | 258.4 ± 15.1[c] | 0.031 |
| 25% (balance TMOS) | 16.2 | 252 ± 20 | 469.0 ± 24.8[c] | 0.025 |
| 40% (balance TMOS) | 24.9 | 196 ± 25 | 240.7 ± 17.9[c] | 0.064 |
| 40% (balance TMOS) | 16.2 | 293 ± 24 | 404.8 ± 28.2 | 0.045 |
| 75% (balance TMOS) | 32.5 | 279 ± 49 | 431.2 ± 29.5 | 0.043 |
| 75% (balance TMOS) | 24.9 | 363 ± 51 | 507.6 ± 30.8 | 0.032 |
| 85% (balance TMOS) | 32.5 | 440 ± 84 | 696.2 ± 44.4 | 0.042 |

[a]Size calculated from scanning electron micrographs of n = 120 particles
[b]Sizes acquired from dynamic light scattering measurements in pH 7.4 PBS for n = 3 syntheses
[c]Ethanol used as dispersant Of note, PBS was used as a dispersant for compositions with a large concentration of MPTMS. However, smaller particles with a large degree of inorganic character (i.e., ≤40 mol % MPTMS) rapidly aggregated in this dispersant and caused erratic DLS measurements. This aggregation may be attributed to a large surface density of protonated silanol groups leading to unfavorable particle interaction. While basic conditions resulted in inconsistent DLS measurements due to particle dissolution, ethanol was a viable alternative dispersant as evidenced by the correlation between DLS and SEM measurements.

Elemental analysis was used to characterize the composition of the particles. As expected, the weight percentages of sulfur in the particles increased accordingly with the MPTMS mol % used to make the particles indicating incorporation of the thiol functionality (Table 2).

TABLE 2

| Particle composition (mol % MPTMS) | Water content (M) | Sulfur content[a] (wt %) |
|---|---|---|
| 75% (balance TEOS) | 32.5 | 13.83 ± 3.01 |
| 75% (balance TEOS) | 24.9 | 16.01 ± 1.71 |
| 75% (balance TEOS) | 16.2 | 15.62 ± 1.90 |
| 85% (balance TEOS) | 32.5 | 20.02 ± 3.88 |
| 25% (balance TMOS) | 24.9 | <0.0[b] |
| 25% (balance TMOS) | 16.2 | 0.51 ± 0.36 |
| 40% (balance TMOS) | 24.9 | 1.09 ± 0.58 |
| 40% (balance TMOS) | 16.2 | 3.08 ± 2.57 |
| 75% (balance TMOS) | 32.5 | 18.29 ± 5.34 |
| 75% (balance TMOS) | 24.9 | 15.30 ± 5.32 |
| 85% (balance TMOS) | 32.5 | 20.55 ± 5.70 |

[a]Average weight percents are calculated from n = 3 syntheses
[b]Weight percent was less than instrument limit of detection Syntheses promoting the formation of discrete, spherical particles tended to be preferentially derived from one precursor as evidenced by a large gap in the transition from 40 to 75 mol % MPTMS (wt % 3.08±2.57 and 15.62±1.90, respectively). These values were in marked contrast to the sulfur wt % of the colloidal silica. Although the increased sulfur wt % were more linearly proportional for the colloidal silica, the lack of discrete, spherical particles was not ideal. The comparison of the two systems (colloidal vs. discrete particles) and syntheses reveals that a balance exists between silane incorporation and certain design criteria.

Example 5

Synthesis of Particles with NAPTMS

Procedure for 25% NAPTMS Balance TMOS/TEOS:
1. Dissolved 85.4 mg NAPTMS (tertiary precursor) in 3.95 mL of ethanol by vortexing
2. To the reaction mixture added 4.09 mL of water then added TMOS/ethanol mixture (71.9 μL TMOS and 200 μL ethanol) via syringe pump at a rate of 1.0 mL/min.
3. Added 6 mL of 5M HCL and let sonicate (120%) for 1 hour.
4. Added 4 mL of ammonium hydroxide and allowed to sonicate (120%) for 30 minutes.

Final Concentrations TMOS and TEOS Particles:

[Silane] = 0.0352M
[Water] = 42.8M
[HCl] = 1.57M
[Ethanol] = 3.85M
[NH3] = 3.43M Size Characterization:

| Particle Composition | Particle size (nm) SEM | Z-average size (nm) DLS | PDI |
|---|---|---|---|
| 25% NAPTMS balance TMOS | 802.8 ± 116 | 607.3 ± 28.9 | 0.17 ± 0.072 |
| 25% NAPTMS balance TEOS | 820.2 ± 95 | 760.6 ± 27.3 | 0.16 ± 0.038 |

Example 6

Nitrosation of Mercaptosilane-Based Silica Particles

Thiols within the particles were nitrosated via reaction with nitrous acid. 12 Particles (~200 mg) were first added to 4 mL methanol (MeOH). While stirring, 2 mL of hydrochloric acid (5 M) was added to the suspension. A 2 mL aqueous solution containing sodium nitrite (2× molar excess to thiol) and DTPA (500 μM) was then added to the particle suspension, and the mixture stirred for 2 h in the dark and on ice. Particles were collected by centrifugation at 4500 rpm (5 min), washed with 40 mL chilled 500 μM DTPA(aq), recollected, washed with 40 mL chilled MeOH, recollected, and vacuum dried for 30 min while shielded from light. Particles were stored at −20° C. in vacuo until further study.

The MPTMS-modified particles were nitrosated to enable NO storage and release. Briefly, the particles were treated with acidified sodium nitrite, generating nitrous acid, a nitrosating agent that reacts with thiols to form RSNOs (see Eq 1).

$$RSH + HNO_2 \rightleftarrows RSNO + H_2O \quad (1)$$

Since S-nitrosothiols prepared from primary thiols absorb light at 330-350 and 550-600 nm, successful RSNO formation was confirmed by the resulting red color of the particles after nitrosation. Furthermore, the intensity of the color increased with MPTMS mol % indicating greater RSNO formation.

Figure 8:
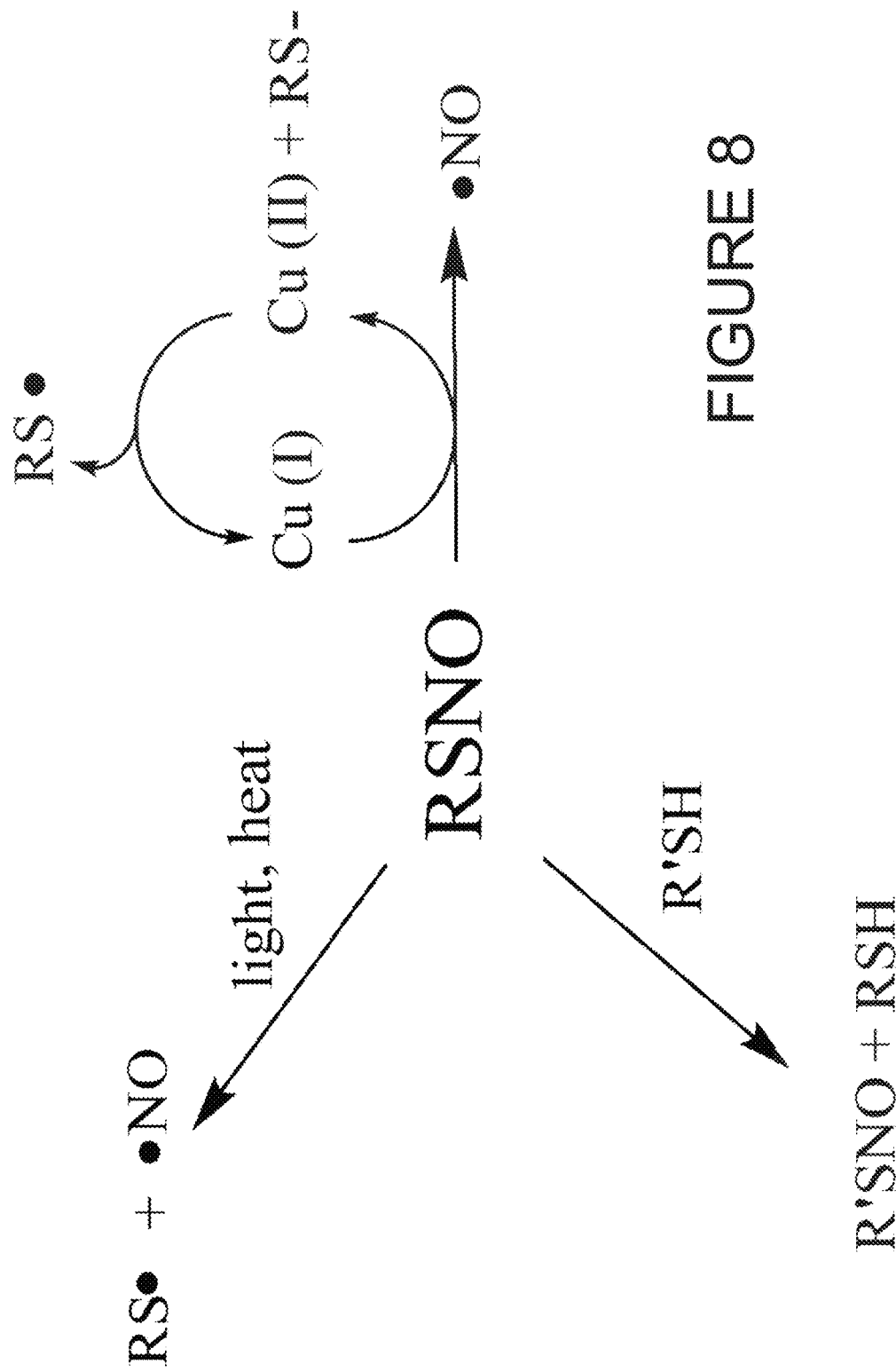
FIG. 8 shows a schematic for the S-nitrosothiol decomposition pathways.

As widely known, S-nitrosothiols decompose via a multitude of pathways (FIG. 8). Both photo and thermal irradiation of RSNOs result in homolytic cleavage of the S—N bond, yielding NO and a thiyl radical. The thiyl radical may subsequently react with an RSNO to generate a disulfide and an additional equivalent of NO. Cu(I), resulting from the reduction of Cu(II) via trace thiolate ions, has been shown to be active in a catalytic RSNO decomposition mechanism. Transnitrosation between a thiol and an RSNO may also occur, resulting in the transfer of the nitroso functionality and formation of a new RSNO species that may decompose via the aforementioned pathways.

Figure 9:
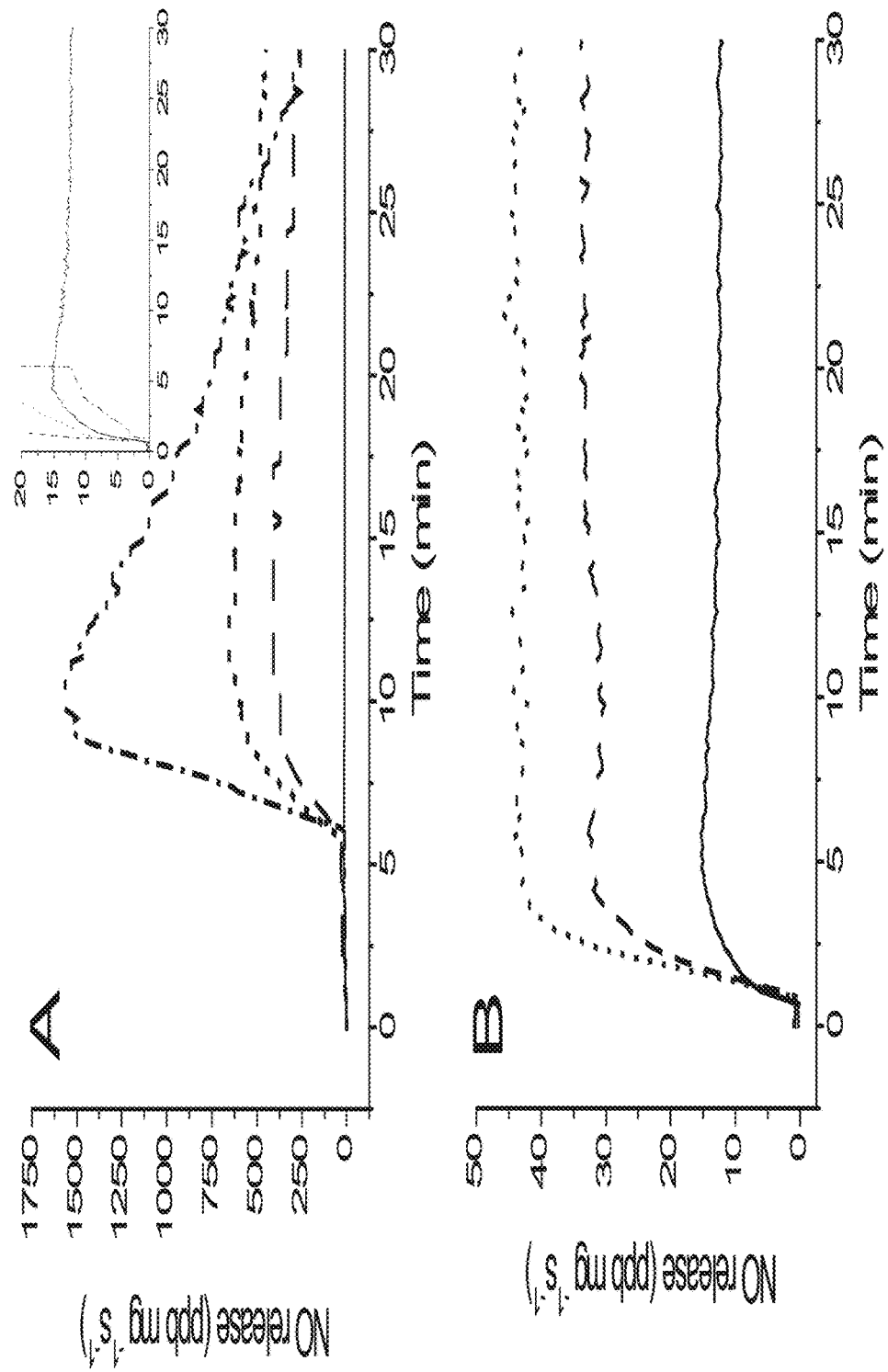
FIG. 9 shows the nitric oxide release from RSNO-modified 75 mol % MPTMS (balance TEOS) particles in the presence of (A) 0 (-), 60 (--), 100 (• • •), and 200 (-•) W irradiation at 0° C. and (B) 0 (-), 10 (--), and 25 (• • •) µM $CuBr_2$/PBS solution at 0° C. Note: 0 µM $CuBr_2$ is 500 µM DTPA (pH 7.4 PBS). The inset of A provides an enlarged view of NO release profile without irradiation.

To assess the NO storage and release, RSNO-modified particles (~2 mg) were added to 500 μM DTPA (pH 7.4 PBS) at a temperature of 0° C., while measuring the ensuing NO release as a function of photolytic decomposition. As shown in FIG. 9A, RSNO-modified silica particles exhibited photo-initiated NO release upon exposure to broadband, white light. Greater irradiation levels (i.e., power) resulted in elevated NO release from the particles. Of note, low levels of NO release (~15 ppb mg$^{-1}$ s$^{-1}$) were observed at 0° C. and in the dark (FIG. 9A inset). Others have shown that oxygen may react with NO to form dinitrogen trioxide ($N_2O_3$), an oxidant that also decomposes RSNOs. Elimination of oxygen from the storage environment of the RSNO-modified particles would thus be expected to increase the NO storage stability of the particles. Indeed, no significant loss in NO release capacity was measured upon storing the particles for 2 months at −20° C. in vacuo and in the dark.

Due to the rapid kinetics of the photo-initiated decomposition, total NO storage of the particles was assessed by exposing the particles to 200 W of broadband light. Indeed, >95% of the NO stored was released after 5 h of irradiation at 200 W. As given in Table 3, the total NO released from the particles ranged from 0.09-4.39 μmol mg$^{-1}$. These levels of NO storage are an order of magnitude larger than previously reported RSNO-modified silica particles. Using the average sulfur weight percents in conjunction with the average NO storage values, the percent conversion of thiol to RSNO for the different particle compositions was calculated to be 58-78% for the 75 and 85 mol % MPTMS/TMOS and MPTMS/TEOS systems. The 25 and 40 mol % MPTMS particles were found to have lower thiol to RSNO conversions (54-63%).

TABLE 3

| Particle composition (mol % MPTMS) | Water content (M) | Total NO released[a] (μmol mg$^{-1}$) |
|---|---|---|
| 75% (balance TEOS) | 32.5 | 3.24 ± 0.61 |
| 75% (balance TEOS) | 24.9 | 3.58 ± 0.39 |
| 75% (balance TEOS) | 16.2 | 3.15 ± 0.60 |
| 85% (balance TEOS) | 32.5 | 3.95 ± 0.66 |
| 25% (balance TMOS) | 24.9 | 0.09 ± 0.02 |
| 25% (balance TMOS) | 16.2 | 0.10 ± 0.02 |
| 40% (balance TMOS) | 24.9 | 0.34 ± 0.02 |
| 40% (balance TMOS) | 16.2 | 0.52 ± 0.22 |
| 75% (balance TMOS) | 32.5 | 3.31 ± 0.85 |
| 75% (balance TMOS) | 24.9 | 3.73 ± 0.62 |
| 85% (balance TMOS) | 32.5 | 4.39 ± 0.02 |

[a]Averages are calculated from n = 3 syntheses and after 5 h of 200 W irradiation The effect of copper on NO release was investigated as a function of copper concentration. These assays were performed using Cu(II) via CuBr$_2$ due to the insolubility of Cu(I) compounds in aqueous solutions. As expected, the NO release from the RSNO-modified particles correlated with the copper concentration (FIG. 9B) with the greatest copper concentration examined (25 μM) generating the maximum NO release (~45 ppb mg$^{-1}$ s$^{-1}$).

The use of RSNO-modified particles for biomedical application likely necessitates an NO release trigger other than light or large concentrations of free copper ions. We thus evaluated NO release from the particles via thermal degradation at 37° C. using 75 mol % MPTMS (balance TEOS, 718.0±51.7 nm) as a model system. Particles were introduced into 500 μM DTPA (pH 7.4 PBS), maintained at 37° C. and shielded from external light while monitoring NO release over 48 h (Table 4). Under these conditions, the particles released a total of 1.17 μmol NO mg$^{-1}$ with a corresponding half life of 2.95 h. When compared to the total amount released after 5 h using 200 W irradiation (3.15 μmol mg$^{-1}$, Table 3), the discrepancy may be attributed to inability to measure NO at low levels beyond 48 h and/or loss of NO through its reaction with oxygen present in the soak solutions. As evident by a pink hue, the particles still contained a portion of their NO payload even after 48 h of release.

TABLE 4

| Time (h) | Instantaneous NO release (ppb mg$^{-1}$ s$^{-1}$)[a] |
|---|---|
| 0 | 1205.7 ± 22.4 |
| 0.5 | 481.2 ± 7.7 |

TABLE 4-continued

| Time (h) | Instantaneous NO release (ppb mg$^{-1}$ s$^{-1}$)[a] |
|---|---|
| 1 | 355.7 ± 7.7 |
| 6 | 74.9 ± 0.7 |
| 12 | 33.2 ± 0.4 |
| 24 | 12.6 ± 0.2 |
| 48 | 2.50 ± 0.07 |

[a]Averages are calculated from n = 3 syntheses

Example 7

Thermal Initiated NO Release Characterization of Primary and Tertiary RSNO Particles For each particle composition, approximately 3 mg of particles were added to the collection flask containing PBS (500 μM DTPA) and the NO release monitored over 75 min. The NO storage and release characteristics are shown in Table 5.

TABLE 5

| Particle Composition | t[NO]total (μmol mg$^{-1}$) at 75 minutes | [NO]$_m$max NO release (pmol mg$^{-1}$) | time to get to max (min) |
|---|---|---|---|
| 75% MPTMS balance TEOS (primary RSNO) | 0.878 | 262 | 1.6 |
| 25% NAPTMS balance TMOS (tertiary RSNO) | 1.70 × 10$^{-3}$ | 0.913 | 32 |
| 25% NAPTMS balance TEOS (tertiary RSNO) | 4.13 × 10$^{-4}$ | 1.31 | 75 |

The NO storage and release characteristics of the 25% NAPTMS sample while under irradiation were also investigated. Using 200 W illumination, and 0.3 m distance, the results are shown in Table 6.

TABLE 6

| Particle Composition | t[NO]total (μmol mg$^{-1}$) at 75 minutes | [NO]$_m$max NO release (pmol mg$^{-1}$) | t to get to max (min) |
|---|---|---|---|
| 25% NAPTMS balance TMOS (tertiary RSNO) | 0.205 | 61.5 | 10.5 |

The results shown in Tables 5 and 6 shown that NO stability of the particles can be significantly increased by using a tertiary nitrosothiol-functionalized silica particles.

Example 8

Influence of Particle Sonication Before/after Nitrosation

Experiment 8A: Nitrosated Particles No Sonication
1. Nitrosate 15 mg of particles in methanol, 5M HCl, and 2 mol X (vs. thiol) of NaNO2/500 uM DTPA.
2. Collect and wash with cold dtpa and cold methanol. Dry under vacuum for 45 min in dark (covered with foil).
3. Add 1 mg of nitrosated particles to 5 mL PBS (DTPA)

4. Expose to 200 W illumination (30 cm from inside bottom of box)

Experiment 8B: Particle Nitrosation then Sonication
1. Nitrosate 15 mg of particles in methanol, 5M HCl, and 2 mol X (vs. thiol) of NaNO2/500 uM DTPA.
2. Collect and wash with cold dtpa and cold methanol. Dry under vacuum for 45 min in dark (covered with foil).
3. Add 1 mg of nitrosated particles to 5 mL of PBS (DTPA) and sonicate for 30 min on ice at amplitude=50%.
4. Expose to 200 W illumination (30 cm from inside bottom of box)

Experiment 8C: Particle Sonication (30 Min at Amplitude=50%) then Nitrosation
1. Sonicate 15 mg of non-nitrosated particles in 4 mL of Methanol on ice for 30 minutes on ice at amplitude=50%.
2. Nitrosatesonicated particles in 4 mL of methanol, 5M HCl, and 2 mol X (vs. thiol) of NaNO2/500 uM DTPA.
3. Collect and wash with cold dtpa and cold methanol. Dry under vacuum for 45 min in dark (covered with foil).
4. Add 1 mg of nitrosated particles to 5 mL PBS (DTPA)
5. Expose to 200 W illumination (30 cm from inside bottom of box)

Experiment 8D: Particle Sonication (60 Min at Amplitude=50%) then Nitrosation
1. Sonicate 15 mg of non-nitrosated particles in 4 mL of Methanol on ice for 60 minutes on ice at amplitude=50%.
2. Nitrosatesonicated particles in 4 mL of methanol, 5M HCl, and 2 mol X (vs. thiol) of NaNO2/500 uM DTPA.
3. Collect and wash with cold dtpa and cold methanol. Dry under vacuum for 45 min in dark (covered with foil).
4. Add 1 mg of nitrosated particles to 5 mL PBS (DTPA)
5. Expose to 200 W illumination (30 cm from inside bottom of box)

The results of Experiments 8A-8D are shown in

| Experiments (see above) | Total NO Concentration ($\mu$mol mg$^{-1}$) | Duration of NO Release (h) | No. of Experiments |
| --- | --- | --- | --- |
| 7A | 1.46 ± 0.16 | 24 | N = 3 |
| 7B | 1.05 ± 0.13 | 24 | N = 3 |
| 7C | 1.38 ± 0.37 | 24 | N = 3 |
| 7D | 1.36 ± 0.23 | 24 | N = 3 |

Figure 10:
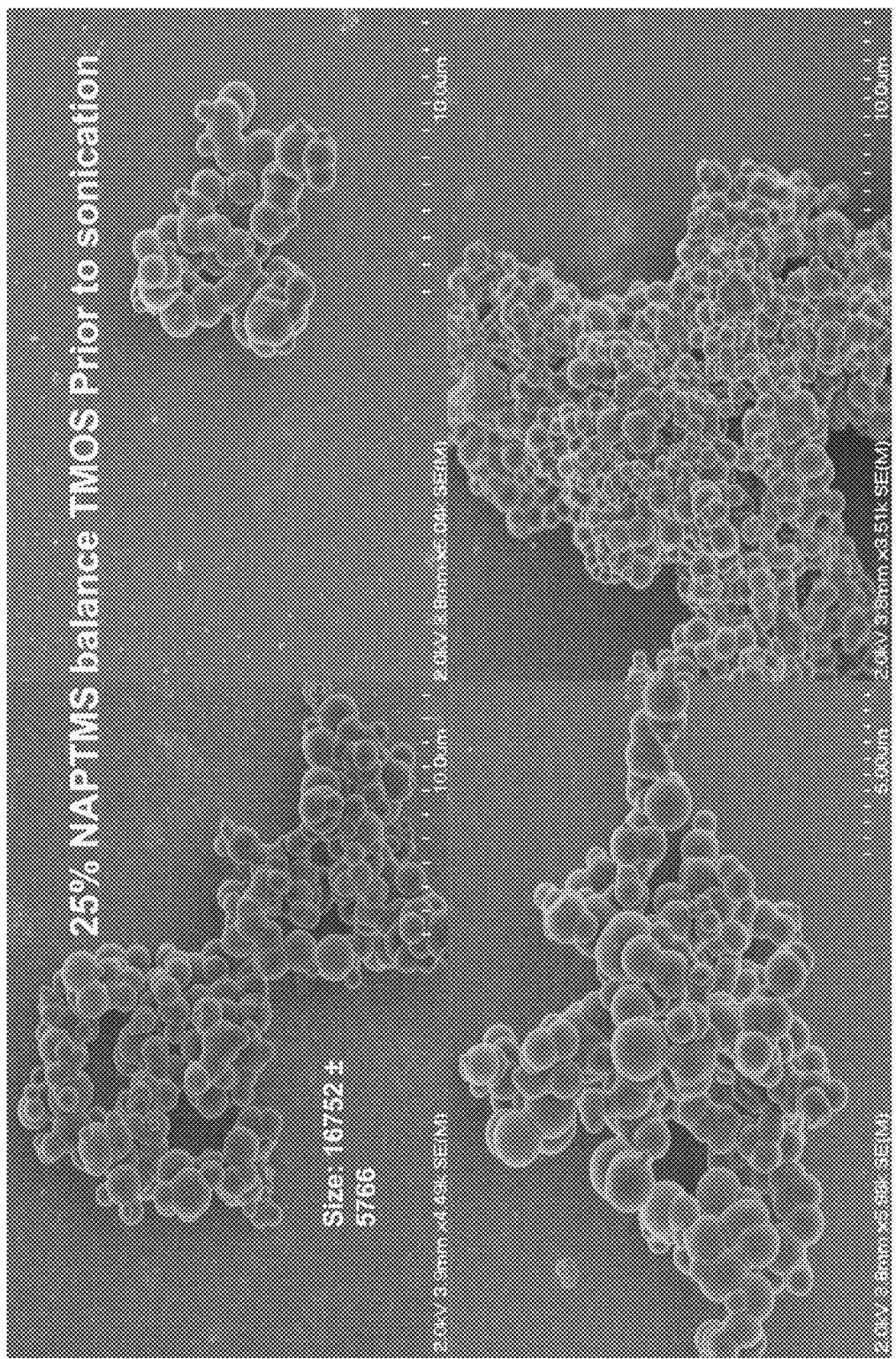
FIG. 10 shows SEM images of tertiary thiol-functionalized co-condensed silica particles according to some embodiments of the invention prior to sonication.
Figure 11:
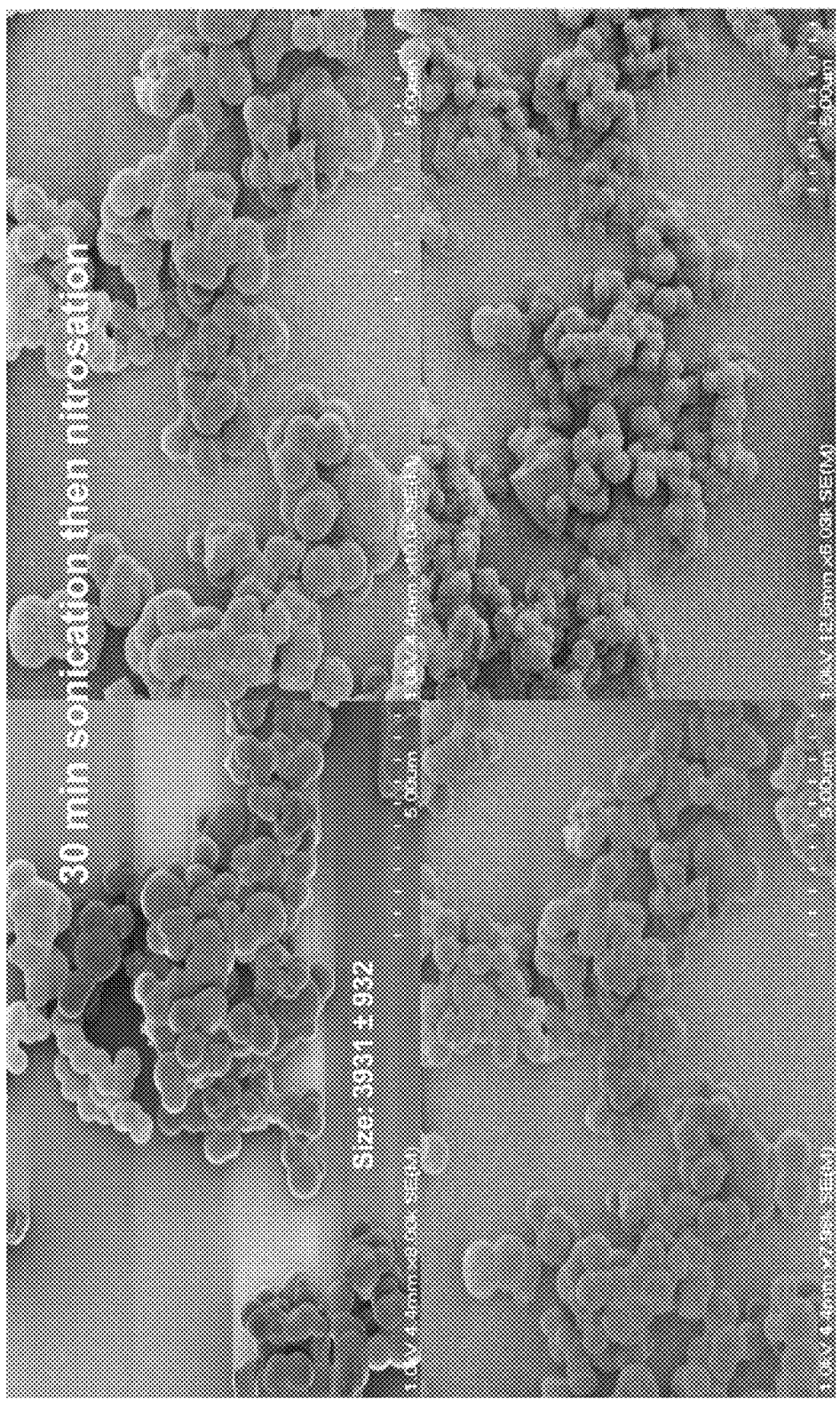
FIG. 11 shows SEM images of tertiary thiol-functionalized co-condensed silica particles according to some embodiments of the invention after 30 minutes sonication followed by nitrosation.
Figure 12:
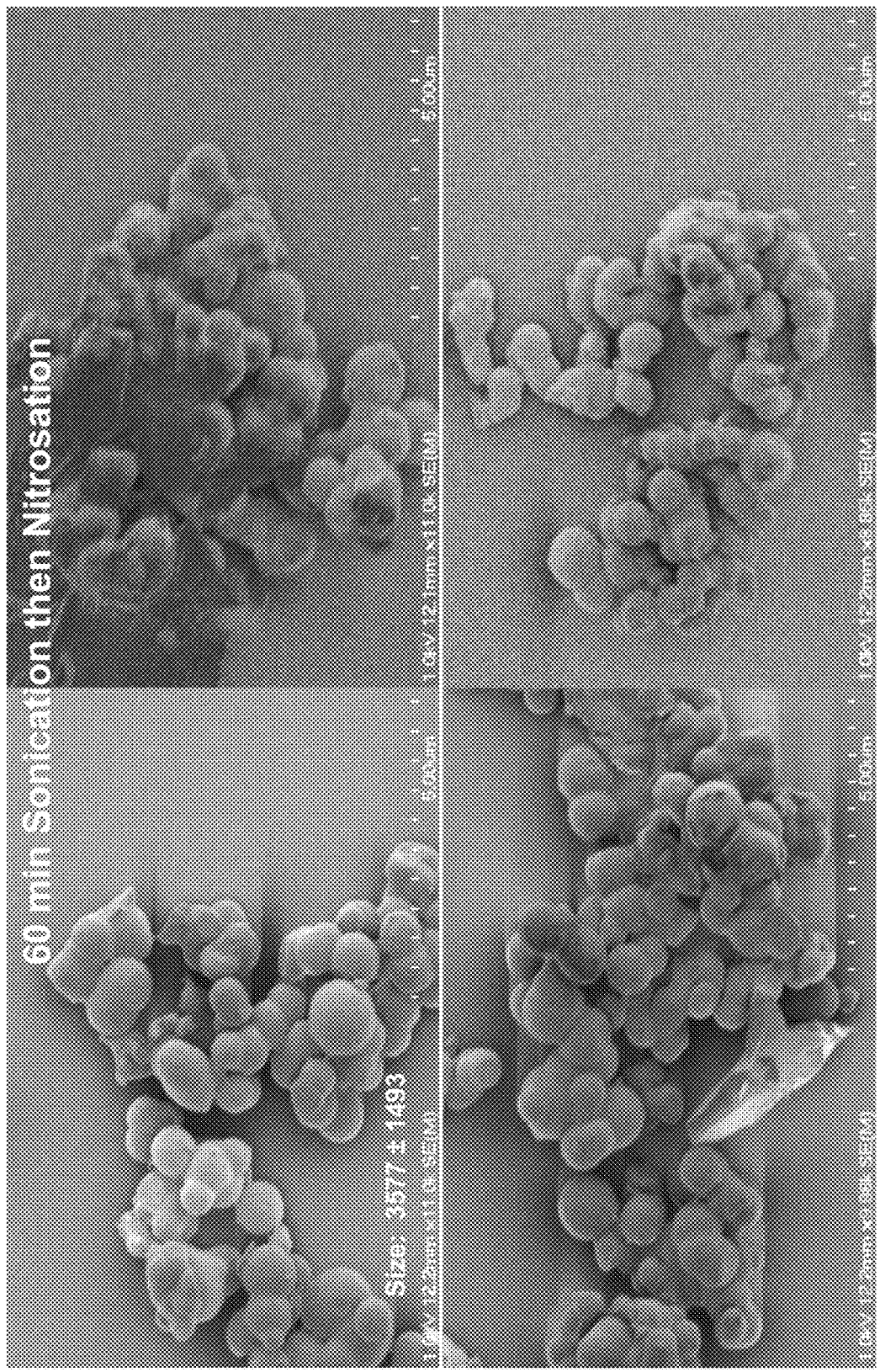
FIG. 12 shows SEM images of tertiary thiol-functionalized co-condensed silica particles according to some embodiments of the invention after 60 minutes sonication followed by nitrosation.

SEM images of the particles formed in Example 7A are provided in FIG. 10. SEM images of the particles formed in Example 7C are provided in FIG. 11. SEM images of the particles formed in Example 7D are shown in FIG. 12. These results show that particle morphology and nitric oxide storage is not significantly influenced by the sonication procedure. Thus, sonicating particles may be used to narrow size distribution and/or making smaller particles.

In the drawings and specification, there have been disclosed embodiments of the invention and, although specific terms are employed, they are used in a generic and descriptive sense only and not for purposes of limitation, the scope of the invention being set forth in the following claims.

We claim:

1. S-nitrosothiol-functionalized co-condensed silica particles having an NO storage in a range of about 0.01 µmol to about 10 µmol NO per mg particle.

2. The S-nitrosothiol-functionalized co-condensed silica particles of claim 1, wherein the particles have an NO storage in a range of about 0.09 µmol to about 4.40 µmol NO per mg particle.

3. The S-nitrosothiol-functionalized co-condensed silica particles of claim 1, wherein the particles comprise a polysiloxane matrix and have at least some nitrosothiol functional groups distributed within the polysiloxane matrix.

4. The S-nitrosothiol-functionalized co-condensed silica particles of claim 1, wherein the S-nitrosothiol functional groups comprise primary nitrosothiol functional groups.

5. The S-nitrosothiol-functionalized co-condensed silica particles of claim 1, wherein the S-nitrosothiol functional groups comprise tertiary nitrosothiol functional groups.

6. S-nitrosothiol-functionalized monodisperse co-condensed silica particles having an average particle diameter in a range of about 200 nm to about 700 nm.

7. The S-nitrosothiol-functionalized co-condensed silica particles of claim 6, wherein the particles comprise a polysiloxane matrix and have at least some nitrosothiol functional groups distributed within the polysiloxane matrix.

8. The S-nitrosothiol-functionalized co-condensed silica particles of claim 6, wherein the S-nitrosothiol functional groups comprise primary nitrosothiol functional groups.

9. The S-nitrosothiol-functionalized co-condensed silica particles of claim 6, wherein the S-nitrosothiol functional groups comprise tertiary nitrosothiol functional groups.

10. The S-nitrosothiol-functionalized co-condensed silica particles of claim 6, wherein the particles are formed from the condensation of a thiol-containing silane and a backbone alkoxysilane.

11. The S-nitrosothiol-functionalized co-condensed silica particles of claim 10, wherein the thiol-containing silane is a tertiary thiol-containing silane.

12. A method of forming the S-nitrosothiol-functionalized monodisperse co-condensed silica particles of claim 6, the method comprising:
    reacting a thiol-containing silane and a backbone alkoxysilane in a sol precursor solution that comprises water to form thiol-functionalized co-condensed silica particles, wherein the thiol-functionalized co-condensed silica particles comprise a polysiloxane matrix and at least some of thiol groups are present within the polysiloxane matrix; and
    reacting the thiol-functionalized co-condensed silica particles with a nitrosating agent to provide the S-nitrosothiol-functionalized monodisperse co-condensed silica particles.

13. The method of claim 12, wherein the thiol-containing silane comprises a primary thiol-containing silane.

14. The method of claim 13, wherein the primary thiol-containing silane is mercaptopropyltrimethoxysilane and the backbone alkoxysilane is tetraethoxysilane.

15. The method of claim 13, wherein the primary thiol-containing silane comprises mercaptopropyltrimethoxysilane and the backbone alkoxysilane comprises tetramethoxysilane.

16. The method of claim 15, wherein the sol precursor solution comprises an ammonia catalyst at a concentration in a range of about 1.9 to about 5.5 M;
    wherein the total silane monomer concentration in the sol precursor solution is in a range of about 0.1 M to about 0.4 M;
    wherein the total silane monomer concentration comprises about 25 to about 85 mol % mercaptopropyltrimethoxysilane; and wherein the water is present in the sol precursor solution at a concentration in a range of about 8.0 to about 32.5 M.

17. The method of claim 12, wherein the thiol-containing silane comprises a tertiary thiol-containing silane.

18. The method of claim 17, wherein the tertiary thiol-containing silane comprises a tertiary thiol having the following structure:

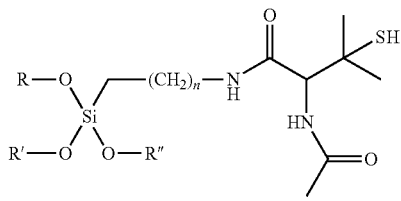

wherein R, R' and R" are each independently alkyl and n is in a range of 0 to 10.

19. The method of claim 18, wherein the tertiary thiol-containing silane has the following structure:

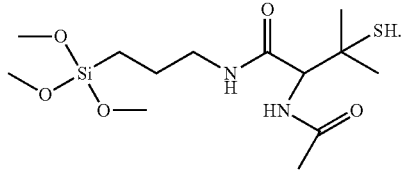 [SMILES: CO[Si](CCCNC(=O)C(NC(C)=O)C(C)(C)S)(OC)OC]

20. The method of claim 18, wherein the backbone alkoxysilane comprises tetraethoxysilane.

21. The method of claim 12, wherein the thiol-functionalized co-condensed silica particles are sonicated prior to reacting the thiol-functionalized co-condensed silica particles with a nitrosating agent.

* * * * *

UNITED STATES PATENT AND TRADEMARK OFFICE
CERTIFICATE OF CORRECTION

PATENT NO. : 9,713,652 B2
APPLICATION NO. : 13/975930
DATED : July 25, 2017
INVENTOR(S) : Schoenfisch et al.

It is certified that error appears in the above-identified patent and that said Letters Patent is hereby corrected as shown below:

On the Title Page

In the References:
(56) References Cited, Page 10, Other Publications, Bonavida B. et al.:
Please correct "*Therapeutic application of nitric oxide rug Resistance Updates*" to read -- *Therapeutic application of nitric oxide Drug Resistance Updates* --

In the Specification

Column 3, Line 13: Please correct "0.5 nit min$^{-1}$." to read -- 0.5 mL min$^{-1}$. --

Column 4, Line 49: Please correct "*J. Colloid Intel face Sci.*" to read -- *J. Colloid Interface Sci.* --

Signed and Sealed this
Twenty-fourth Day of April, 2018

Andrei Iancu
*Director of the United States Patent and Trademark Office*